United States Patent [19]
Vega et al.

[11] Patent Number: 6,153,209
[45] Date of Patent: Nov. 28, 2000

[54] ARTICLE HAVING A TRANSFERABLE BREATHABLE SKIN CARE COMPOSITION THEREON

[75] Inventors: Victor Nicholas Vega, Cincinnati, Ohio; Thomas Robert Hanser, Taylor Mill, Ky.; Tim Van Hauwermeiren, Ramsdonk, Belgium; Donald Carroll Roe, West Chester, Ohio

[73] Assignee: The Procter & Gamble Company, Cincinnati, Ohio

[21] Appl. No.: 09/407,950

[22] Filed: Sep. 28, 1999

[51] Int. Cl.[7] .............................. A01N 25/34; A61L 9/00; A61F 13/15

[52] U.S. Cl. ...................... 424/404; 424/400; 424/76.1; 424/76.3; 424/445; 604/363; 604/364; 604/381; 604/382

[58] Field of Search .................................. 424/404, 76.1, 424/76.3, 445, 400; 604/363; 514/847

[56] References Cited

U.S. PATENT DOCUMENTS

| | | | |
|---|---|---|---|
| 3,489,148 | 1/1970 | Duncan et al. | 128/284 |
| 3,585,998 | 6/1971 | Hayford et al. | 128/284 |
| 3,875,942 | 4/1975 | Roberts et al. | 128/287 |
| 3,896,807 | 7/1975 | Buchalter | 128/261 |
| 3,920,015 | 11/1975 | Wortham | 128/284 |
| 3,935,862 | 2/1976 | Kraskin | 128/287 |
| 3,957,971 | 5/1976 | Oleniacz | 424/70 |
| 3,964,486 | 6/1976 | Blaney | 128/284 |
| 4,034,077 | 7/1977 | Hill et al. | 424/69 |
| 4,273,786 | 6/1981 | Kraskin | 424/319 |
| 4,478,853 | 10/1984 | Chaussee | 424/358 |

(List continued on next page.)

FOREIGN PATENT DOCUMENTS

| | | |
|---|---|---|
| 0 564 307 A1 | 10/1993 | European Pat. Off. . |
| 0 682 868 A1 | 11/1995 | European Pat. Off. . |
| 0 815 841 A1 | 1/1998 | European Pat. Off. . |
| 2660552 A1 | 10/1991 | France . |
| 2675341 A1 | 10/1992 | France . |
| 2680448 A1 | 2/1993 | France . |
| 4136540 A1 | 5/1992 | Germany . |
| 019249 | 2/1984 | Japan . |
| 057105 | 3/1984 | Japan . |
| 104286 | 5/1985 | Japan . |
| 61-28078 | 2/1986 | Japan . |
| 280893 | 11/1988 | Japan . |
| 2-31756 | 2/1990 | Japan . |
| 02129110 | 5/1990 | Japan . |
| 4-182423 | 6/1992 | Japan . |
| 07118691 | 10/1993 | Japan . |
| 07118691 | 5/1995 | Japan . |
| 408003333 | 1/1996 | Japan ............................. C08J 5/18 |
| 10-175843 | 6/1998 | Japan . |
| WO 98/03147 | 1/1998 | WIPO . |

OTHER PUBLICATIONS

Article from Fragrance Journal 1997–10, pp. 105–110, entitled A Study on the Skin Surface Lipids of New–Born Baby and Its Application to Cosmetics (Translated by Ralph McElroy Co.).

Article from Manufacturing Chemist Magazine, Jun. 1996 issue, entitled Softening skin with emollient ingredients.

Article from Raw Materials Magazine, entitled "Emollients and emolliency in skincare products".

*Primary Examiner*—Thurman K. Page
*Assistant Examiner*—Isis Ghali
*Attorney, Agent, or Firm*—Caroline Wei-Berk; George W. Allen; Kirsten K. Stone

[57] ABSTRACT

The present invention relates to an article having a skin care composition disposed on at least a portion of the article. The skin care composition is a breathable, barrier protectant which can be immobilized on the article and is transferable to the wearer's skin via contact, normal wearer motion and/or body heat. Particularly, the skin care composition should have a water vapor transmission rate of at least about 0.1 gm/m$^2$/hr and a barrier property of at least about −25 on Hunter b scale, as measured by a Methylene Blue Dye Method.

32 Claims, 3 Drawing Sheets

U.S. PATENT DOCUMENTS

| | | | |
|---|---|---|---|
| 4,556,560 | 12/1985 | Buckingham | 424/145 |
| 4,623,339 | 11/1986 | Ciraldo et al. | 604/359 |
| 4,657,537 | 4/1987 | Zimmerer | 604/360 |
| 4,685,909 | 8/1987 | Berg et al. | 604/360 |
| 4,690,821 | 9/1987 | Smith et al. | 424/401 |
| 4,753,643 | 6/1988 | Kassai | 604/359 |
| 4,760,096 | 7/1988 | Sakai et al. | 514/847 |
| 4,790,836 | 12/1988 | Brecher | 604/359 |
| 4,842,593 | 6/1989 | Jordan et al. | 604/360 |
| 4,959,059 | 9/1990 | Eilender et al. | 604/358 |
| 4,970,220 | 11/1990 | Chaussee | 514/358 |
| 4,996,239 | 2/1991 | Matravers | 514/873 |
| 5,053,229 | 10/1991 | Hattori et al. | 424/572 |
| 5,091,193 | 2/1992 | Enjolras et al. | 424/642 |
| 5,110,593 | 5/1992 | Benford | 424/401 |
| 5,192,277 | 3/1993 | Chung et al. | 604/360 |
| 5,194,261 | 3/1993 | Pichierri | 424/401 |
| 5,215,759 | 6/1993 | Mausner | 424/489 |
| 5,362,488 | 11/1994 | Sibley et al. | 424/78.05 |
| 5,409,903 | 4/1995 | Polak et al. | 514/23 |
| 5,415,649 | 5/1995 | Watanabe et al. | 604/385.2 |
| 5,436,007 | 7/1995 | Hartung et al. | 424/402 |
| 5,466,396 | 11/1995 | Madison et al. | 252/557 |
| 5,508,034 | 4/1996 | Bernstein | 424/401 |
| 5,525,346 | 6/1996 | Hartung et al. | 424/402 |
| 5,607,760 | 3/1997 | Roe | 442/375 |
| 5,609,587 | 3/1997 | Roe | 604/360 |
| 5,618,529 | 4/1997 | Pichierri | 424/78.06 |
| 5,631,012 | 5/1997 | Shanni | 424/401 |
| 5,635,191 | 6/1997 | Roe et al. | 424/402 |
| 5,643,588 | 7/1997 | Roe et al. | 424/402 |
| 5,653,970 | 8/1997 | Vermeer | 424/70.24 |
| 5,674,509 | 10/1997 | Date et al. | 424/401 |
| 5,871,763 | 2/1999 | Luu et al. | 424/402 |
| 5,968,025 | 10/1999 | Roe et al. | 604/364 |

ARTICLE HAVING A TRANSFERABLE BREATHABLE SKIN CARE COMPOSITION THEREON

FIELD OF THE INVENTION

The present invention relates to absorbent articles such as diapers, training pants, adult incontinence devices, sanitary napkins, pantiliners, and the like. More particularly, the present invention relates to absorbent articles for body exudates wherein the article has a skin care composition disposed thereon. Such a composition is transferable to the wearer's skin by normal contact, wearer motion, and/or body heat. The skin care composition used in the present invention is suitable for maintaining and/or improving skin condition of the wearer of the article upon transfer during use. The skin care composition used in the present invention provides a protective barrier against water, large molecules and particulate matter that exist in body exudates. Such a composition also minimizes abrasions where the absorbent article and the wearer's skin are in contact, eases BM clean-up, and may also deliver skin care ingredients to achieve various skin benefits. Most importantly, the skin care composition used in the present invention provides a breathable, protective barrier that keeps body exudates and other irritants from direct contact with the skin yet allows water vapor to pass through.

BACKGROUND OF THE INVENTION

The major function of disposable absorbent products, such as diapers, training pants, adult incontinence devices, sanitary napkins, panty liners, and the like, is to absorb and contain body exudates. Although these absorbent articles may be highly efficient for the absorption of liquids, they also can create an occlusive micro-environment in the body regions where they are worn. This occlusion micro-environment often results in overhydration of the skin. It is known that overhydrated skin is more susceptible to skin disorders, including erythema (i.e., redness), diaper rash or diaper dermatitis, heat rash, abrasion, pressure marks and skin barrier break-down. Diaper rash is a common form of irritation and inflammation of those parts of an infant's body normally covered by a diaper, which is caused by one or more of the following factors: moisture, occlusion, chafing, continued contact with urine, feces, or both, or mechanical or chemical irritation (see 21 C.F.R. 333.503). When absorbent articles are worn to absorb and contain the body exudates, the skin under the absorbent articles is held in direct contact with body exudates and other irritants, under an occluded condition. Often, the skin is subjected to such condition for extended periods of time, that is, until the soiled article is changed. As the skin under the absorbent article becomes overhydrated or irritated by such prolonged and repeated exposures, the skin condition is compromised, i.e., the skin becomes more susceptible to skin disorders or damages. While this condition is best known in infants, it is not limited to infants. Similar conditions occur with, for example, incontinent or bed-ridden adults.

To address the concerns of skin abnormalities associated with wearing absorbent articles, the practical approaches often attempt to address multiple causes or important cofactors. Reducing skin overhydration by frequent changing of diapers, the use of moisture absorbing powders, the use of superabsorbent materials, and the improvement of air flow in diapers are some of the well known approaches.

A typical approach is to apply a topical cream, ointment, lotion or paste by hand to the buttocks, genitals, anal and/or other regions before placing the absorbent article on the wearer. This procedure usually provides some degree of physical barrier protection to the skin against direct contact with urine, feces or other irritants. However, the barrier approach may be occlusive in itself. It has been found that occlusive barrier material may interfere with the healing and repair of skin's natural barrier function once skin barrier function is compromised or skin disorders have developed.

It is recognized that a skin care composition for skin disorders associated with skin overhydration should have good barrier properties. Petrolatum is a well known barrier protectant which forms a water repellant layer on the skin surface and minimizes moisture loss from the skin. Petrolatum also forms a barrier against large molecules (e.g., fecal enzymes) and particulate matters in body exudates. But this petrolatum layer over skin is occlusive such that it may interfere with the barrier repair capability of the skin. Lanolin is another good barrier protectant as well as a nourishing substance, but lanolin is also occlusive. Many other fats and oils derived from natural sources, such as plants or animals, have been shown to have nourishing and/or occlusive properties, but they often are oxidatively unstable and require hydrogenation or stabilizers. However, hydrogenation tends to increase the viscosity of the substance and reduce its spreadability, and stabilizers may cause other skin problems, such as irritation or allergy.

Another well known barrier substance derived from nature is "vernix caseosa" or "vernix caevsa" (hereinafter "vernix"), which is the substance that covers the entire body of human and mammalian fetuses at or near full term. Vernix on fetal skin exhibits some unique characteristics not found in fully developed or mature skin. It has been shown that vernix has a very low transepidermal water loss (TEWL) value. It is believed that vernix helps the new born infant maintain body temperature by reducing water loss, which is accompanied by heat loss, from the epidernis. Vernix is also a very effective barrier against moisture penetration. Mature skin becomes overhydrated and develops maceration or irritant dermatitis after just a couple of days' exposure to water. In contrast, the full or near term fetus' skin is healthy, smooth and supple, even though is has been exposed to the total immersion environment in the uterus for an extended period of time. Moreover, vernix is a naturally occurring substance that has none of the side effects such as irritation, sensitization and allergy.

Various skin creams, lotions and ointments are available for treating skin disorders. Most of them are moisturizing preparations that enhance water retention in the skin, and thus, are not effective for skin disorders associated with overhydration, such as erythema or diaper rash. However, skin preparations for overhydration problem have been focused mostly on the barrier approach. Hence these preparations tend to be occlusive and hinder the natural barrier repair function of the skin. Moreover, the lotions, creams or ointments have always been applied by hand to the targeted areas. The topical application by hands tends to leave a thick sticky coating or a layer of white residue that is aesthetically unpleasing. This procedure is also wasteful, messy, time-consuming and often forgotten.

Attempts have also been made to prepare absorbent articles which contain a transferable skin care composition on the skin-capacity surface so that the hand-application procedure is not necessary. However, many lotions, creams and ointments generally are not suitable for delivery via an absorbent article because they are fluid or substantially mobile at room temperature. These fluid and mobile substances do not remain localized on the surface of the article but instead may migrate into the interior of the article. Accordingly, these substances can interfere with the absorbency of the interior core layer of the article due to their hydrophobic, barrier properties.

Also a higher level of such compositions must be applied to the article surface in order to provide enough transfer to the skin to achieve a protective coating. This higher add-on level not only increases the cost per article, but also increases the possibility of migration into and through the packaging or wrapper materials, creating an article that smears and leaks greasy substances.

U.S. Pat. No. 4,760,096 to Sakai et al. teaches a moisturizing skin composition comprising a phosphatide (such as lecithin) and one or more C10–C30 carboxylic acid sterol esters. Such compositions preferably contain a caprylic/capric acid triglyceride for enhanced moisturization. A major disadvantage of the composition disclosed by Sakai is that the composition is a moisturizer which enhances the water retention in the skin. Accordingly, it does not prevent or minimize the overhydration problem of the skin under an absorbent article.

U.S. Pat. No. 5,409,903 to Polak et al. teaches a method and a composition for treatment or prevention of skin rash or dermatitis wherein urease containing bacteria, bacterial components and by-products are implicated. The composition may be applied to skin in combination with an adhesive, film-forming or barrier compound. A major disadvantage of Polak et al. is that a thin film coating is required to achieve water vapor or gas permeability, and the composition is only effective as a barrier against enzymes or large particulate materials.

U.S. Pat. No. 3,896,807 to Buchalter teaches an skin-contacting article impregnated with a solid oil phase of a cream formulation which forms a cream upon addition of moisture thereto. A major disadvantage of the article disclosed by Buchalter is that the substance is an occlusive barrier protectant. Another disadvantage of Buchalter is that the transfer of a beneficial substance from the article to the skin is delayed until fluids are absorbed by the solid oil phase.

U.S. Pat. No. 3,489,148 to Duncan et al. teaches a disposable diaper comprising a "hydrophobic and oleophobic" topsheet wherein a portion of the topsheet is coated with a discontinuous film of oleaginous substance. A major disadvantage of the of the diaper disclosed by Duncan et al. is that the hydrophobic and oleophobic topsheet is slow in promoting transfer of urine to the underlying absorbent core.

U.S. Pat. No. 5,643,588 to Roe et al. teaches an absorbent article having a skin treating composition on the surface of a disposable diaper that is solid or semi-solid at ambient temperature, and is transferable to the wearer's skin by contact, wearer motion and/or body heat. However, some of the compositions disclosed by Roe et al. may be occlusive.

In light of the foregoing, it would be desirable to have an article-deliverable skin care composition that is breathable or non-occlusive. Such a skin care composition should also have good barrier properties against urine, feces, or other body exudates or irritants. Such composition should also minimize skin overhydration, maintain the integrity of skin barrier function, and thus effectively prevent secondary irritation or infection when skin is compromised or damaged, and promote the barrier repair function of the skin.

Moreover, it would be desirable that the skin care composition can be immobilized on an absorbent article for hands-free transfer to the wearer's skin during use, for minimizing adverse effects on the absorbency of the article, and for avoiding stains on clothing, bedding or packaging.

It would also be desirable for the skin care composition not to irritate or sensitize the skin and be oxidatively stable for long shelf life of the product.

It would be further desirable to have an absorbent article having a breathable, barrier type skin care composition disposed thereon for hands-free transfer to the wearer's skin by contact, normal wearer motion and/or body heat.

It would also be desirable to have an absorbent article having one or more types of skin care composition disposed thereon, wherein at least a portion of the composition is transferable to the wearer's skin to provide desired skin benefits including a prevention and/or reduction in erythema, a reduction in BM adherence to the skin for easier removal of BM, reduction in occlusion, overhydration and/or abrasion of the skin, and the like.

It would also be desirable to have a skin care composition which is solid or semi-solid at ambient temperature so that it is immobilized on the surface of an absorbent article. The skin care composition should be able to become fluid or plastic at or near skin temperature, or when slight force is applied, so that it is readily transferable to the skin. The skin care composition should also be substantially flowable at the processing temperature so that it can be successfully applied to the article surface, i.e., without tearing or otherwise damaging the article.

SUMMARY OF THE INVENTION

The present invention relates to articles having a skin care composition disposed on at least a portion of the article. The skin care composition provides a breathable, barrier protectant, can be immobilized on the article and is transferable to the wearer's skin via contact, normal wearer motion and/or body heat. Particularly, the skin care composition is solid or semi-solid at 20° C., and a Water Vapor Permeation Rate of at least about 0.1 gm/m$^2$/hr, and a barrier property of at least about −25 on Hunter b-scale, as measured by a Methylene Blue Dye Method.

It has been found that the water vapor permeability of such composition can be enhanced by adding agents such as branched esters, branched hydrocarbons, polysiloxanes, phospholipids or mixtures thereof, while maintaining barrier property and immobility/transferability characteristics of the composition.

DETAILED DESCRIPTION OF THE INVENTION

1. Definitions

Figure 1:
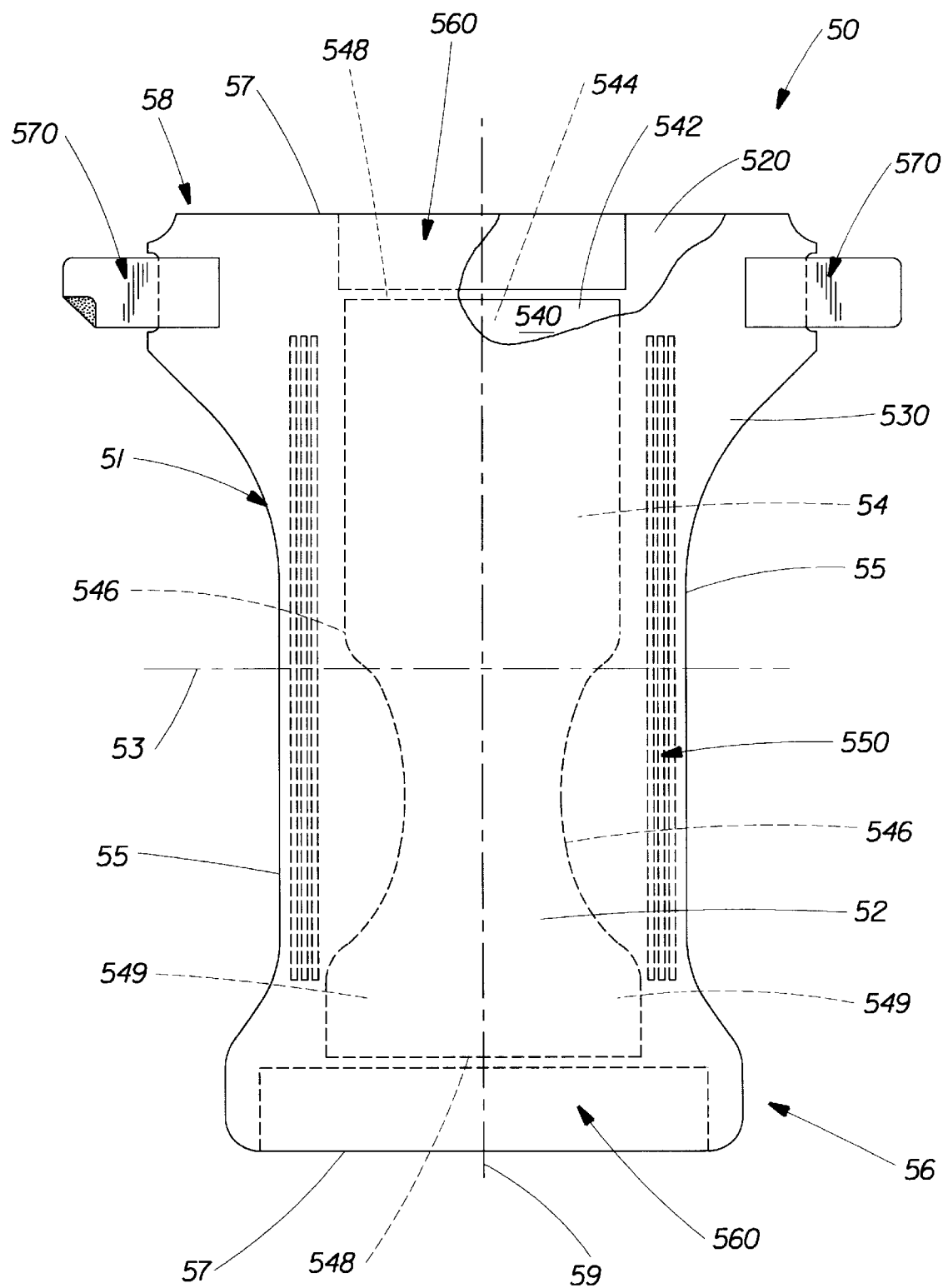
FIG. 1 shows an absorbent article in the form of a diaper according to the present invention.

As used herein, the term "comprising" means that the various components, ingredients, or steps can be conjointly employed in practicing the present invention. Accordingly, the term "comprising" encompasses the more restrictive terms "consisting of" and "consisting essentially of".

As used herein, the term "occluded skin" means skin in areas under an absorbent article when the article is worn, As used herein, the term "compromised skin" is not limited to a particular area of the body; the term "compromised skin" means skin that has been subjected to repeated or chronic exposures, or one or more acute episodes of exposure, to body exudates (e.g., urine, feces, menstrual fluids, sweat), moisture, irritants, etc. such that the skin develops redness, chaffing, roughness, wrinkled appearance or itchiness.

As used herein, the term "absorbent articles" means diapers, training pants, sanitary napkins, pantyliners, incontinence articles, diaper holders, and the like.

As used herein, the term "skin care agent" means a substance or a mixture of substances, when applied to a subject's skin, either alone or incorporated into a skin care composition, provides skin condition benefits such as actual or perceived changes in appearance, cleanliness and attractiveness. The term is also directed to substances that soothe, calm, or promote feelings of relief when applied to the skin, e.g., herbal, mineral or aromatic ingredients.

As used herein, the term "effective amount" of the skin care composition means an amount large enough to significantly or positively bring about the desired effect or to modify the condition to be treated such that the skin appears cleaner, more attractive or in better condition. The effective amount varies with the specific ingredient or composition used, the preventative or prophylactic effect desired, the type of condition or problem to be treated, the age and physical condition of the individual being treated, the severity of the condition to be treated, the intensity and duration of the treatment, and like factors.

As used herein, the terms "dermatologically acceptable" or "safe" means the amount of a skin care composition or the components therein is low enough that it produces no undue (i.e., at a reasonable benefit to risk ratio) side effects, such as toxicity, irritation, or allergic response, in a general population.

Other terms are defined herein where initially discussed.

All percentages, ratios and proportions used herein are defined by weight of the composition unless otherwise specified.

II. Absorbent Article

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene garments such as sanitary napkins, panti-liners and tampons, diapers, incontinence briefs, diaper holders, training pants, and the like.

Disposable absorbent articles typically comprise a liquid pervious topsheet, a liquid impervious backsheet and an absorbent core positioned between the topsheet and the backsheet. Disposable absorbent articles and components thereof, including the topsheet, backsheet, absorbent core, and any individual layers of these components, have a body facing surface and a garment facing surface. As used herein, "body facing surface" means that surface of the article or component which is intended to be worn toward or adjacent to the body of the wearer, while the "garment facing surface" is on the opposite side and is intended to be worn toward or placed adjacent to the wearer's clothing or undergarments when the disposable absorbent article is worn.

The following description generally discusses the absorbent core, topsheet, and backsheet materials that are useful in disposable absorbent articles of the present invention. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, training pants, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace, carded, wet-laid, melt-blown, hydroentangled, hydroformed, hydroapertured, combinations of the above, or the like.

The backsheet is impervious to liquids (e.g., menses and/or urine) and is preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. The size of the backsheet is dictated by the size of the absorbent core and the exact absorbent article design selected.

As discussed above, while it is preferred that the composition which is continually, automatically transferred to the wearer's skin by wearing articles described herein be relatively impervious to liquids such as urine and runny feces, it is also preferred that the composition be relatively vapor pervious to provide a nonocclusive barrier for the skin. In this regard, to further improve skin condition in the wearer's region under the absorbent articles via the presently disclosed methods, absorbent articles useful in those methods may also provide "breathability", to facilitate relatively lower relative humidity in the area between the skin and the absorbent article. Recently, attempts have been disclosed that are directed to improving wearer skin condition by allowing the overhydrated skin to dehydrate to a more acceptable level by allowing either air to reach the skin (thus minimizing potential occlusion effects) and/or providing means for removing water vapor from the surface of the skin. Generally, such features are referred to as providing "breathability" or "vapor or moisture permeability". Specific examples include feminine hygiene products, such as catamenial products or so-called pantyliners as described in EP-A-0.104.906; EP-A-0.171.041; EP-A-0.710.471; the disclosure of each of which is incorporated herein by reference. Such products generally have relatively low liquid storage capacity when compared, for example, to baby diapers or adult incontinence products, which have theoretical storage capacities more than ten times the capacity of a feminine hygiene product. The "breathable" articles described in these references may be treated with skin care composition as described herein, and such treated articles may be useful in the methods of the present invention.

Such breathable materials can be various kinds of webs, such as films which are rendered air/vapor pervious by aperturing as described in U.S. Pat. No. 5,628,737, which issued in the name of Dobrin, et al. on May 13, 1997, or by exploiting the "microporosity" property as described in EP-A-0.238.200; EP-A-0.288.021; EP-A-0.352.802; EP-A-0.515.501; U.S. Pat. No. 4.713.068, whereby small voids are created within the film similar to very small cracks. WO 94/23107; WO 94/28224; U.S. Pat. No. 4,758,339 which issued in the name of Yeo, et al. on Jul. 19, 1988; and EP-A-0.315.013 all describe alternative breathable materials which can be fibrous textile or non-woven webs, with air/vapor easily penetrating through the relatively large pores of the structure. Such webs, can be either treated or untreated with regard to improving their liquid impermeability properties, such as described in EP-A-0.196.654. In WO 95/16562 a laminate of a non-woven with a breathable film is disclosed. Further disclosures such as in WO 95/16746 relate to other materials allowing water molecules to diffuse through. Also, combinations of various materials comprising various layers of any of the above elements are also well known. Absorbent articles using any of the approaches described in these references (each of which is incorporated herein by reference) in combination with delivering a composition as described herein may be used to form the article of the present invention. Indeed, a particularly preferred absorbent article for use in the present methods is described in detail in co-pending U.S. patent application Ser. No. 08/926,566, filed Sep. 10, 1997 by Elder et al., the disclosure of which is incorporated herein by reference.

The backsheet and the topsheet are positioned adjacent the garment facing surface and the body facing surface, respectively, of the absorbent core. The absorbent core is preferably joined with the topsheet, the backsheet, or both in any manner as is known by attachment means (not shown in FIG. 1) such as those well known in the art. However, embodiments of the present invention are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-203 1. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the wearer-contacting surface is treated with a skin care composition comprises diapers and training pants. As used herein, the term "diaper" refers to an absorbent article generally worn by infants, and incontinent persons, that is worn about the lower torso of the wearer. In other words, the term "diaper" includes infant diapers, training pants, adult incontinence devices, etc.

FIG. 1 is a plan view of the diaper 50 useful on one embodiment of the present invention in its flat-out, uncontracted state (i.e., with elastic induced contraction pulled out) with portions of the structure being cut-away to more clearly show the construction of the diaper 50 and with the portion of the diaper 50 which faces away from the wearer (the outer surface) oriented towards the viewer. As shown in FIG. 1, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550; an elastic waist feature multiply designated as 560; and a fastening system generally multiply designated as 570.

The diaper 50 is shown in FIG. 1 to have an outer surface 52, an inner surface 54 corresponding to the body facing surface which is opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The body facing surface 54 of the diaper 50 comprises that portion of the diaper 50 which is positioned adjacent to the wearer's body during use. The body facing surface 54 generally is formed by at least a portion of the topsheet 520 and other components that may be joined to the topsheet 520, such as leg cuffs 550, as well as any regions to which the topsheet may not extend but which still contact the wearer, such as the waist feature 560, side panels and the like. The outer surface 52 comprises that portion of the diaper 50 which is positioned away from the wearer's body (i.e., the outer surface 52 generally is formed by at least a portion of the backsheet 530 and other components that may be joined to the backsheet 530). The first waist region 56 and the second waist region 58 extend, respectively, from the end edges 57 of the periphery 51 to the lateral centerline 53 of the diaper 50. FIG. 1 also shows the longitudinal centerline 59.

FIG. 1 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; U.S. Pat. No. 5,554,145 issued to Roe et al. on Sep. 10, 1996; U.S. Pat. No. 5,569,234 issued to Buell et al. on Oct. 29, 1996; U.S. Pat. No. 5,580,411 issued to Nease et al. on Dec. 3, 1996; and U.S. patent application Ser. No. 08/915,471 entitled "Absorbent Article With Multi-Directional Extensible Side Panels" filed Aug. 20, 1997 in the name of Roble et al. Each of these patents is incorporated herein by reference. The absorbent cores of diapers described in these patents can be adapted to include an absorbent gelling material therein.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least portions of the upper surface of the topsheet are treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

Alternatively, the topsheet may be in the form of an apertured formed film, which is preferred in feminine hygiene absorbent articles. Apertured formed films are useful because they are pervious to body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued December 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for use in feminine hygiene products is the formed film described in one or more of the above patents and marketed on sanitary napkins by The Procter & Gamble Company of Cincinnati, Ohio as "DRI-WEAVE®."

The body facing surface of the formed film topsheet can be hydrophilic so as to help body liquids to transfer through the topsheet faster than if the body surface was not hydrophilic so as to diminish the likelihood that liquid will flow off the topsheet rather than flowing into and being absorbed by the absorbent structure. In a preferred embodiment, surfactant is incorporated into the polymeric materials of the formed film topsheet such as is described in U.S. S.I.R. No. H1670, "Absorbent Article Having A Nonwoven and Apertured Film Coversheet" by Aziz, et al., published on Jul. 1, 1997, which is incorporated by reference. Alternatively, the body facing surface of the topsheet can be made hydrophilic by treating it with a surfactant such as is described in the above referenced U.S. Pat. No. 4,950,254, incorporated herein by reference.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent materials for use as the absorbent core of articles useful in the present methods are described, e.g., in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized waist bands (not shown) and/or elasticized side panels (also not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference. Absorbent articles having elasticized cuffs that are treated with a composition that may be useful herein are disclosed in co-pending U.S. patent application Ser. No. 08/766,386, filed Dec. 3, 1996 by Schulte et al., U.S. patent application Ser. No. 08/962,310, filed Oct. 31, 1997 by Schulte et al., and U.S. patent application Ser. No. 08/962,312, filed Oct. 31, 1997 by VanRijswijck et al., the disclosure of each is herein incorporated by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; and U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; 5,591,152. Each of these patents is incorporated herein by reference. In alternative embodiments, opposing sides of the garment may be seamed or welded to form a pant. This allows the article to be used as a pull-on diaper or training pant.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Of course, it will be recognized that any absorbent article design may be utilized in the context of the present invention, so long as skin care composition is applied to the article so as to be transferred to the skin during use. The disclosure above is merely for illustrative purposes.

The present invention may also employ training pants to effect delivery of the desired skin care composition. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of which is incorporated herein by reference.

Another disposable absorbent article embodiment of the present invention comprises incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. Pat. No. 5,304,161 issued Apr. 19, 1994 to Noel, et al. The disclosure of each of these references is incorporated herein.

Another disposable absorbent article embodiment of the present invention comprises feminine hygiene articles, such as sanitary napkins. Suitable feminine hygiene articles are disclosed in U.S. Pat. No. 4,556,146, issued to Swanson et al. on Dec. 3, 1985, U.S. Pat. No. 4,589,876, issued to Van Tilberg on Apr. 27, 1993, U.S. Pat. No. 4,687,478, issued to Van Tilburg on Aug. 18, 1997, U.S. Pat. No. 4,950,264, issued to Osborn, III on Aug. 21, 1990, U.S. Pat. No. 5,009,653, issued to Osborn, III on Apr. 23, 1991, U.S. Pat. No. 5,267,992, issued to Van Tilburg on Dec. 7, 1993, U.S. Pat. No. 5,389,094, issued to Lavash et al. on Feb. 14, 1995, U.S. Pat. No. 5,413,568, issued to Roach et al. on May 9, 1995, U.S. Pat. No. 5,460,623, issued to Emenaker et al. on Oct. 24, 1995, U.S. Pat. No. 5,489,283, issued Van Tilburg on Feb. 6, 1996, U.S. Pat. No. 5,569,23 1, issued to Emenaker et al. on Oct. 29, 1996, and U.S. Pat. No. 5,620,430, issued to Bamber on Apr. 15, 1997, the disclosure of each of which is incorporated by reference herein.

III. Skin Care Composition

The skin care compositions used in the articles of the present invention provide various skin benefits intended to maintain and/or improve the skin condition of the skin areas under an absorbent article or chronic exposure to body waste, moisture, irritants, etc. It is preferred that the skin care composition should provide a protective, and preferably non-occlusive function (e.g., a relatively liquid impervious but vapor pervious barrier) to avoid skin overhydration and skin exposure to materials contained in body exudates; an abrasion minimizing function to reduce skin irritation in the areas where the absorbent article is in contact with the wearer's skin; and should contain ingredients that deliver, either directly or indirectly, skin care benefits. For example, direct benefits may be directed towards overhydration reduction, redness reduction or skin conditioning, and indirect benefits may be directed towards removal or reduction of skin irritants in body exudates. It is also preferred that the skin care composition contains emollients that maintain or improve the skin condition against chaffing, roughness, wrinkled appearance or itchiness. Furthermore, the skin care composition preferably has a smooth, silky, non-grainy skin feel to minimize abrasion of sensitive or compromised skin due to conditions such as chaffing, roughness, or rashes.

The preferred skin care composition for use in the present invention should contain sufficient emollients so that it maintains skin in its normal, healthy condition or improves the skin condition against chaffing, roughness, redness, wrinkled appearance or itchiness. Specifically, the preferred composition should contain emollients that are barrier protectants against overhydration and external irritants, their derivatives or by-products, particularly those existing or developed in body exudates. Barrier protection is particularly effective in preventing skin abnormalities and damages associated with overhydration, and subsequent break-down of skin's protective barrier function. The preferred composition should also contain non-occlusive or breathable (i.e., water vapor and gas permeable) agents so that the skin covered by the composition is subjected to a local environment closely simulating that of untreated skin, i.e., the treated skin can "breathe" like the untreated skin. Breathability is an important factor in the healing of overhydrated and/or damaged skin and maintaining skin appearance or condition. It is surprising to find that the skin care compositions used in the present invention can achieve both barrier protection and breathability to provide an optimal environment for diapered skin.

Because the skin care composition is applied to the skin via a delivery vehicle such as an absorbent article, the preferred skin care composition for the present invention should have a melting/rheological profile that meets the following requirements: the composition should preferably be solid or semi-solid at room temperature (i.e., about 20° C.) so that "migration" on the substrate surface and the adverse effects to the absorbency of the article are minimized; the preferred composition should also be readily transferable to the skin by contact, normal wear motions and/or body heat; therefore, the skin care composition is preferably plastic or fluid at skin temperature (i.e., about 34–36° C.) to facilitate the transfer to the skin; and the preferred composition should have storage stability, typically up to at least about 45° C.

Typically, the skin care compositions used in the present invention will have a breathability of at least about 0.1 gm/m$^2$/hr, preferably at least about 1 gm/m$^2$/hr, and more preferably at least about 10 gm/m$^2$/hr, as measured by the collagen water vapor transmission rate (WVTR) test, which is described in the Test Methods Sections hereinafter.

The skin care compositions used in the present invention should also have a moisture barrier property ranging from about 5 to about –25, preferably from about 5 to about –15, more preferably from about 5 to about –5, as measured on the Hunter's "b" coordinate, using a Methylene Blue Dye Method described in the Test Methods Section hereinafter. As measured by this Method, a skin care composition having a poorer water barrier property would give a larger negative "b" value.

As will be discussed hereinafter, the skin care compositions useful in the present invention will generally have a melting profile such that they are relatively immobilized and localized on the wearer-contacting surface of the article at room temperature, are readily transferable to the skin at skin temperature, and yet are not completely liquid under "stressful" storage conditions. Preferably, the compositions are easily transferable to the skin by way of contact, shear, normal wearer's motions and/or body heat. Because the composition preferably is substantially immobilized on the article's surface, a relatively low level of composition is needed to impart the desired skin care benefits. In addition, special barrier or wrapping materials may be unnecessary in packaging the treated articles useful in the present invention.

The compositions useful herein are generally solid, or more often semi-solid at room temperature, i.e., at 20° C. Being solid or semi-solid at room temperature, such compositions do not have a tendency to flow and migrate to a significant degree to undesired locations of the article, and thus avoid significant interference with the absorbency of the article. This means less skin care composition is required for imparting desirable appearance, protective or conditioning benefits. Preferably, the compositions of the present invention have a zero shear viscosity at room temperature between about 1.0×10$^6$ centipoise and about 1.0×10$^8$ centipoise. More preferably, the zero shear viscosity is between about 5.0×10$^6$ centipoise and about 5.0×10$^7$ centipoise.

The term "semisolid", as used herein, means that the composition has a rheology typical of pseudoplastic or plastic liquids. When no shear is applied, the compositions can have the appearance of a semi-solid but can be made to flow as the shear rate is increased. Without intending to be bound by theory, it is believed that while such compositions contain primarily solid components, they also include some liquid components.

To enhance the immobility of the preferred compositions, the viscosity of the formulated compositions should be as high as necessary to prevent substantial flow within the article to undesired locations. One the other hand, too high a viscosity may inhibit transfer of composition to the skin.

Therefore, a balance should be achieved so the viscosities are high enough to keep the compositions localized on the surface of the article, but not so high as to impede transfer to the skin. In addition, the compositions preferably have a final melting point above skin temperature, more preferably above potential "stressful" storage conditions that can be greater than 45° C. (e.g., warehouse in Arizona, car trunk in Florida, etc.). Specifically, preferred compositions will have the following melt profile:

| Characteristic | Preferred Range | Most Preferred |
|---|---|---|
| % liquid* at room temp. (20° C.) | 2–50 | 3–25 |
| % liquid* at body temp. (37° C.) | 25–95 | 30–90 |
| final melting point (° C.) | ≧38 | ≧45 |

The skin care compositions useful in the present invention will generally comprise an emollient or mixture of emollients, a permeability enhancing agent and an immobilizing agent. Other optional ingredients may also be included, such as skin care agents, theological agents, antioxidants, and the like.

A. Emollients

As used herein, the term "emollient" means a material that protects against wetness or irritation, softens, soothes, supples, coats, lubricates, moisturizes, protects and/or cleanses the skin. In a preferred embodiment, these emollients will have either a plastic or liquid consistency at ambient temperatures, i.e., 20° C.

Emollients may maintain the normal, healthy skin condition. Emollients may also improve the dry skin condition by restoring its moisture level as well as its softness, smoothness and flexibility. One type of emollients, generally referred to as moisturizers or moisturizing emollients, attract moisture from the surrounding atmosphere and enhance the water absorption of the stratum corneum (i.e., the outer, corny layer of the skin). Another type of emollients, generally referred to as barrier protectants, form an occlusive (i.e. non-water-permeable) layer when deposited on the surface of the skin, which prevent or retard moisture losses from the deeper layers of the skin to the atmosphere. These emollients also act as barriers protecting the skin from larger molecules, such as fecal matter, enzymes, and other irritants.

Representative barrier protectant type emollients useful in the present invention include, but are not limited to, petroleum-based emollients; fatty acid esters; fatty alcohol emollients; alkyl ethoxylate emollients; fatty alcohol ethers; polyol polyesters; glyceryl esters; free sterols, sterol esters and their derivatives; triglycerides and derivatives; sphingolipids; vegetable or animal oils; hydrogenated vegetable oils; kaolin and its derivatives; vitamins such as $B_3$ (niacinamide), C (ascorbic acid), $D_3$, E (tocopherol), E ester (tocopheryl nicotinate); or mixtures of these emollients.

Suitable petroleum-based emollients include paraffins, i.e., hydrocarbons or mixtures of hydrocarbons; particularly preferred are hydrocarbons having chain lengths of from 16 to 32 carbon atoms. Petroleum-based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are preferred emollients for compositions of the present invention. Petrolatum is particularly preferred because of its good barrier property (based on the Methylene Blue Test described hereinafter). When employed, petrolatum comprises no less than about 15 wt %, preferably no less than about 20 wt %, more preferably no less than about 30 wt % of the skin care composition.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids (e.g., lactic acid), such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{22}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Suitable fatty alcohol ether type emollients include ethers derived from $C_{12}$–$C_{18}$ fatty alcohols or $C_{12}$–$C_{18}$ fatty alcohols and lower alcohols.

Suitable fatty ester type emollients also include polyol polyesters, particularly the "liquid" polyol polyesters which has a complete melting temperature at or below body temperature (i.e., about 37° C.). Exemplary polyols include, but are not limited to, polyhydric alcohols such as pentaerythritol; sugars such as raffinose, maltodextrose, galactose, sucrose, glucose, xylose, fructose, maltose, lactose, mannose and erythrose; and sugar alcohols such as erythritol, xylitol, malitol, mannitol and sorbitol. Such polyols are esterified with fatty acids and/or other organic radicals having at least 2 carbon atoms and up to 30 carbon atoms. While it is not necessary that all of the hydroxyl groups of the polyol be esterified, preferred polyol polyester emollients of the present invention have substantially all (e.g., at least about 85%) of the hydroxyl groups esterified. Particularly preferred are sucrose polyol polyesters such as sucrose polycottonate, sucrose polysoyate, and sucrose polybehenate. Mixtures of such polyol polyesters are also suitable emollients for the present invention. Other suitable polyol polyesters are disclosed in U.S. Pat. No. 5,609,587, issued to Roe on Mar. 11, 1997, and in U.S. Pat. No. 5,607,760, issued to Roe on Mar. 4, 1997, the disclosure of each is incorporated herein by reference. Other ester materials are further described in U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Also useful herein are various $C_1$–$C_{30}$ monoesters and polyesters of glycerin and derivatives thereof, including glyceride, acetoglycerides, and ethoxylated glycerides of $C_{12}$–$C_{28}$ fatty acid, triethylene glycol, and derivatives thereof. These esters are derived from glycerin and one or more carboxylic acid moieties. Depending on the constituent acid and glycerin, these esters can be in liquid, semi-solid or solid form at room temperature. Solid or semi-solid glyceryl esters are also suitable for use herein as immobilizing agents. Nonlimiting examples include glyceryl tribehenate, glyceryl stearate, glyceryl palmitate, glyceryl distearate, glyceryl dipalmitate, and the like.

Also useful herein are sphingolipids, such as ceramides, sphingosines, phytosphingosines, and the like.

An effective emollient having superior barrier properties may be a mixture of components which simulate the skin's natural water-barrier forming lipid complex, particularly vernix (i.e., the substance covering the bodies of fetuses or newborns of human or other mammals). A preferred emollient is a simulate of vernix in a mixture of sterols, sterol esters and triglycerides. However, other substances occurring naturally in the stratum corneum are also preferred, such as sodium pyrrolidone carboxylic acid, sodium lactate/ lactic acid, free fatty acids. L-proline, guanidine, pyrrolidone, ceramide, and urea. Other emollients derived from natural sources are also suitable for use herein, such as hydrolyzed protein and other collagen-derived proteins; keratin and derivatives; acetamide MEA, and the like.

A preferred emollient for use herein comprises (based on the total weight of the emollient in the skin care composition):

(i) triglycerides ranging from about 1 to about 90 wt %, preferably from about 5 to about 50 wt %, more preferably from about 10 to about 25 wt %;

(ii) sterols ranging from about 1 to about 40 wt %, preferably from about 3 to about 30 wt %, more preferably from about 5 to about 20 wt %;

(iii) sterol esters ranging from about 1 to about 90 wt %, preferably from about 5 to about 50 wt %, more preferably from about 10 to about 25 wt %; and (iv) petroleum-based emollient from about 1 to about 90%, preferably from about 5 to about 50 wt %, more preferably from about 10 to about 25 wt %.

Nonlimiting examples of triglycerides suitable for use herein are typically alkanoic triglycerides, and other triglycerides that exist in vegetable or animal oils. A particularly preferred triglyceride is capric/caprylic triglyceride mixtures, available as Myritol® 318, from Henkel Corp., Ambler, Pa.

Vegetable oils and hydrogenated vegetable oils and waxes are also useful herein. Some of the fully or partially hydrogenated vegetable oils may be solid or semi-solid (i.e., having a waxy consistency) at ambient temperature. Nonlimiting examples of vegetable oils and hydrogenated vegetable oils and waxes include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, jojoba oil, tea tree oil, avocado oil, olive oil, canola oil, their hydrogenated products, cocoa butter, shea butter, and mixtures thereof Also useful herein are animal oils such as shark liver oil, cod liver oil, and the like.

Nonlimiting examples of sterols suitable for use herein include cholesterol, ergosterol, sitosterol, cholecalciferol, and other sterols found in phytosterols, soy sterols or tall oil sterols; lanosterols and other sterols found in lanolin and hydrogenated lanolin; and derivatives thereof, such as acetylated lanolin (available as Acylan® from Croda Inc., Parsippany, N.J.). Since high concentration of sterols tends to crystallize at cold spots along the processing equipment, the sterols are typically used in combination with the petroleum-based emollients, such as petrolatum, at a weight ratio of sterol to petrolatum from about 1:1 to about 1:4, preferably from about 1:1 to about 1:3.

Nonlimiting examples of sterol esters suitable for use herein include stearate, palmitate, acetate, lanolate, macadamiate, nonanoate, oleate, butyrate, hydroxystearate, isostearate, sulfate, isostearate carbonate of cholesterol and other sterols. A particularly preferred sterol esters is a mixture of $C_{10}$–$C_{30}$ carboxylic acid esters of sterols, which is predominantly a cholesterol/lanosterol mixture (available as Super Sterol Ester® from Croda, Inc., Parsippany, N.J.). Super Sterol Ester® is derived from wool wax by a process disclosed in part in U.S. Pat. No. 4,138,416 issued to Koresawa et al., which is incorporated herein by reference.

The emollient component of the compositions used in the present invention should preferably be substantially anhydrous. As used herein, the term "substantially anhydrous" means the emollients or mixtures thereof typically has a water content of less than about 10%, preferably less than about 5%, more preferably less than about 1%, and most preferably less than about 0.5% by weight of the emollient component. The substantially anhydrous character of the emollients avoids overhydration of the already susceptible skin which is chronically exposed to a high relative humidity micro-environment. Furthermore, the substantially anhydrous character of the emollients avoids the wicking effect of the highly absorbent core, which may preferentially draw the emollient components towards the core, interfering with the absorbency of the core and keeping the emollients away from the topsheet surface and the wearer's skin.

The amount of emollient included in the composition will depend on a variety of factors, including the particular emollient involved, the skin benefits desired, the other components in the composition, and like factors. The emollients will generally comprise from about 5 to about 95 wt % of the skin care composition. Preferably, the emollients comprise from about 10 to about 90 wt %, more preferably from about 20 to about 80 wt %, and most preferably from about 30 to about 75 wt %, of the skin care composition.

B. Permeability Agents

Typically, the skin care compositions of the present invention will also include a permeability agent. The permeability agent is a substance which, when incorporated in a composition, increases the water vapor permeation from the skin or collagen film surface through the composition that covers it. Preferably the permeability agent is also miscible with the emollients of the present invention.

Representative permeability agent useful in the present include branched or unsaturated fatty acid esters, such as branched chain aliphatic esters derived from C1–C30 alcohols and C1–C30 mono- or di- carboxylic acids; C7–C40 branched hydrocarbons; polysiloxanes; phospholipids; and mixtures thereof.

Branched fatty acid esters suitable for use herein may have branching in the acid chain, the alcohol chain, or both. Branching also has the effect of lowering the melting temperature of the fatty acid esters such that the fatty acid esters suitable for use herein may be liquids at room temperature. Fatty acid esters suitable for use herein may also have unsaturation in the acid chain, the alcohol chain, or both. Branched or unsaturated structures within the fatty acid esters have been found to be effective to increase WVTR of the skin care composition, therefore, are effective as permeability agents. However, unsaturation in the chain structure often leads to oxidative instability, which may require the incorporation of stabilizers or antioxidants. Certain stabilizers or antioxidants may cause skin irritation or sensitization in some individuals. Where unsaturated permeability agents are used, antioxidants such as vitamin E and derivatives are preferred because of their non-irritating and/or non-sensitizing characters. Nonlimiting examples of antioxidants suitable for use herein are ascorbic acid, tocopherol, tocopherol acetate, and mixed tocopherol (available as COVI-OX T-50 or T-70 from Henkel, Ambler, Pa.).

Particularly preferred fatty acid ester permeability agents are derived from C8–C22 fatty alcohols and C8–C22 fatty acids, including branched and/or unsaturated alcohols, branched and/or unsaturated acids, and mixtures thereof. Nonlimiting examples of fatty acid esters useful herein include diisopropyl adipate (available as Ceraphyl 230 from ISP Van Dyk, Belleville, N.J.), octyldodecyl stearoyl stearate, isononyl isononanoate (available as Salacos 99 from Ikeda Corp., Island Park, N.Y.), isostearyl isononanoate, octyl palmitate, octyl hydroxystearate, stearyl heptanoate, ceterayl octanoate, butyl octanol, 2-ethylhexyl-12-hydroxy stearate, decyl oleate, dioctyl adipate, dioctyl succinate, isocetyl stearate, octyl cocoate, octyl palmitate, and mixtures thereof.

Also useful herein as permeability agents are C7–C40 branched hydrocarbons, such as isoparaffins, squalane, squalene, and the like. Squalene, being the partially unsaturated form of squalane, is oxidatively unstable and may require incorporation of anti-oxidants such as those described above.

Other suitable types of permeability agents for use herein include polysiloxane compounds. In general, suitable polysiloxane materials for use in the present invention include those having monomeric siloxane units of the following structure:

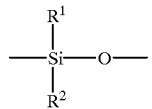

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities. Preferably, the polysiloxane suitable for use as permeability agents herein has a branched, cyclic and/or unsaturated structure in at least one of the R radicals.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are tolyl, xylyl, ethylphenyl, and the like. Exemplary aryl radicals are benzyl, α-phenylethyl, β-phenylethyl, α-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluoroethyl, fluoroethyl, trifluoroethyl, trifluorotloyl, hexafluoroxylyl, and the like.

In a preferred embodiment, the permeability agent may be a substituted polymethylsiloxane wherein at lease one substituent is a functional group selected form the group consisting of methyl, phenyl, amino, other alkyl, carboxyl, hydroxyl, ether, polyether, aldehyde, ketone, amide, ester, thiol, and mixtures thereof. Particularly preferred for use herein is polydimethylsiloxane.

Viscosity of polysiloxanes useful for the present invention may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only.

Particularly suitable for use as permeability agents in the compositions of the present invention are polysiloxane compounds having long linear alkyl groups or phenyl groups, including phenyl-functional polymethylsiloxane compounds (e.g., Dow Corning 556 Cosmetic-Grade Fluid: polyphenylmethyl siloxane) and cetyl or stearyl functionalized dimethicones such as Dow 2502 and Dow 2503 polysiloxane waxes, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred. Other preferred polysiloxane compounds for use in the present invention are disclosed in U.S. Pat. No. 5,059,282 (Ampulski et al), issued Oct. 22, 1991, which is incorporated herein by reference.

Nonlimiting examples of phospholipids suitable for use herein as permeability agents include a material selected from the group consisting of lecithin, cephalin, phosphatidylserine, phosphatidylinositol, phosphatidic acid, sphingomyelin, and mixtures thereof. Lecithin is available in its pure form or in mixtures with oils and other components (from American Lecithin, Oxford, Conn.). Soy lecithin and egg lecithin are mixtures containing lecithin and are also suitable for use herein.

The amount of permeability agent included in the composition will depend on a variety of factors, including the particular emollients and/or immobilizing agents involved, the skin benefits desired, the other components, if any, in the composition (e.g., skin care actives), and like factors. The permeability agent will comprise from about 1 to about 95 wt % of the skin care composition. Preferably, the permeability agent will comprise from about 5 to about 75 wt %, and more preferably from about 5 to about 50 wt %, of the skin care composition.

C. Immobilizing Agents

Another optional, preferred component of the skin care compositions useful in the present invention is an agent capable of immobilizing the skin care composition in the desired location in or on the treated article. Because certain of the preferred emollients in the composition have a plastic or liquid consistency at 20° C., they tend to flow or migrate, even when subjected to modest shear. When applied to a wearer-contacting surface or other location of an absorbent article, especially in a melted or molten state, the emollient will not remain primarily in or on the treated region. Instead, the emollient will tend to migrate and flow to undesired regions of the article and adversely affect the absorbency of the article.

Specifically, if the emollient migrates into the interior of the article, it can cause undesired effects on the absorbency of the article core due to the hydrophobic characteristics of many of the emollients and other skin conditioning agents used in the compositions useful in the methods of the present invention. It also means that much more emollient has to be applied to the article to get the desired skin smoothness benefits. Increasing the level of emollient not only increases the cost, but also exacerbates the undesirable effect on the absorbency of the article's core and undesired transfer of composition during processing/converting of the treated articles.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer-contacting surface or in the region to which it is applied.

In addition to being miscible with (or solubilized in) the emollient, the immobilizing agent preferably has a melting profile that will provide a composition that is solid or semisolid at room temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

It is also advantageous to microscopically "lock or entrap" the emollient in the immobilizing agent on the wearer-contacting surface or the region of the article to which the composition is applied. This can be accomplished by using immobilizing agents which tend to form fine crystals or have high crystallinity. Upon cooling, the immobilizing agent forms multiple seeds or nuclei, from which the crystalline structures grow, and entrap the emollients. In addition, outside cooling of the treated article via blowers, fans, cold rolls, etc. can speed up crystallization rate of the immobilizing agent. In this approach, the faster cooling or crystallization rate may be sufficient to overcome the tendency of the components to separate or segregate and to "lock-in" the composition in a substantially homogeneous mixture (i.e., immiscible components can still provide a substantially homogeneous skin care composition suitable for use in the present invention).

Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof Preferred immobilizing agents include $C_{16}$–$C_{22}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated absorbent article.) Cetearyl alcohol (a mixtures of cetyl alcohol and stearyl alcohol) and behenyl alcohol are particularly preferred. Other preferred immobilizing agents include $C_{16}$–$C_{22}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{22}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{22}$ fatty alcohols increase the rate of crystallization of the composition causing the composition to crystallize rapidly onto the surface of the substrate.

Other suitable immobilizing agents that may be used herein include alpha-hydroxy fatty acids and fatty acids having from about 10 to about 40 carbons include 12-hydroxystearic acid, 12-hydroxylauric acid, 16-hydroxyhexadecanoic acid, behenic acid, stearic acid, palmitic acid, oleic acid, linoleic acid, myristic acid, ricinoleic acid, eurcic acid, lauric acid, isostearic acid, and mixtures thereof. Nonlimiting examples of suitable fatty acids are further described in U.S. Pat. No. 5,429,816, issued to Hofrichter et al. on Jul. 4, 1995, and U.S. Pat. No. 5,552,136, issued to Motley on Sep. 3, 1996, disclosure of each is herein incorporated by reference.

Other suitable immobilizing agents are "solid" polyol polyesters having a plastic or solid consistency at or below body temperature (i.e. about 37° C.), and liquid and solid polyol polyester blends that are solid or semi-solid at room temperature. Examples of suitable polyol polyesters for use as immobilizing agents herein are described in U.S. Pat. No. 5,607,760, issued to Roe on Mar. 4, 1997, which is incorporated herein by reference.

Other suitable immobilizing agents that may be used herein include "solid" glyceryl esters (i.e., plastic or solid at or below skin temperature), particularly glyceryl esters having C8–C30 fatty acid chains. Nonlimiting examples of glyceryl esters include glyceryl monoesters, preferably glyceryl monoesters of C16–C22 saturated, unsaturated and branched chain fatty acids such as glyceryl oleate, glyceryl stearate, glyceryl palmitate, glyceryl behenate, and mixtures thereof; and polyglyceryl esters of C16–C22 saturated, unsaturated and branched chain fatty acids, such as polyglyceryl-4 isostearate, polyglyceryl-3 oleate, diglyceryl monooleate, tetraglyceryl monooleate and mixtures thereof.

Other suitable immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin. Suitable polyhydroxy fatty acid esters for use in the present invention will have the formula:

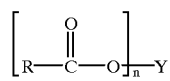

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use as immobilizing agents in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use as immobilizing agents in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di- laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174, 927 to Honsa, issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)—[($CHOH)_{n-1}$]—$CH_2OH$, —$CH_2OH$—$CH_2$—($CHOH)_2$—($CHOR^3$)($CHOH$)—$CH_2OH$, where n is an integer from 3 to 5, and $R^3$ is H or a cyclic or aliphatic monosaccharide. Most preferred are the glycityls where n is 4, particularly —$CH_2$—($CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

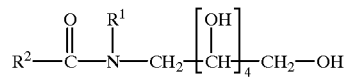

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having hydrophilic lipophilic balance (HLB) values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially uniform mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc., West Babylon, N.Y. Synthetic waxes such as those derived from polyethylene may also be used herein.

Certain polyol polyesters are also suitable for use as immobilizing agents herein, particularly the higher melting polyol polyesters which are solid or semi-solid at room temperature. Examples of solid or semi-solid polyol polyesters are described in Other suitable polyol polyesters are disclosed in U.S. Pat. No. 5,607,760, issued to Roe on Mar. 4, 1997, the disclosure of which is incorporated herein by reference.

The amount of the optional immobilizing agent that can be included in the composition will depend on a variety of factors, including the emollients and permeability agents involved, the particular immobilizing agent involved, if any, the other components in the composition (e.g., skin care actives), whether an emulsifier is required to solubilize the immobilizing agent in the other components, and like factors. When present, the composition will typically comprise from about 5 to about 95% of the immobilizing agent. Preferably, the composition will comprise from about 5 to about 50%, most preferably from about 10 to about 40%, of the immobilizing agent.

D. Other Optional Components

Compositions can comprise other components typically present in emulsions, creams, ointment, lotions, suspensions, etc. of this type. These components include water, surfactants, emulsifiers, skin care agents, humectants, anti-oxidants, viscosity modifiers, suspending agents, pH buffering systems, disinfectants, antibacterial actives, antiviral agents, vitamins, pharmaceutical actives, film formers, perfumes, soothing agents, pigments, deodorants, opacifiers, astringents, solvents, preservatives, and the like. All of these materials are well known in the art as additives for such formulations and can be employed in appropriate amounts in the compositions for use herein.

Depending on the skin condition to be treated, humectants may be included in the skin care compositions. Humectant is a type of moisturizing emollient which attracts moisture from the surrounding atmosphere and enhance water absorption of the stratum comeum (i.e., the outer, corny layer of the skin). Nonlimiting examples of humectants useful herein include glycerin; C2–C6 glycols, such as ethylene glycol, propylene glycol, butylene glycol, hexalene glycol; polyethylene glycols (PEGs), such as PEG-2, PEG-3, PEG-30, and PEG-50; polypropylene glycols (PPGs), such as PPG-9, PPG-12, PPG-15, PPG-17, PPG-20, PPG-26, PPG-30, and PPG-34; glycolic esters and ethers, such as C4–C20 alkylether of PEG or PPG, C1–C20 carboxylic acid esters of PEG or PPG, di-C8–C30 alkyl ethers of PEG or PPG; sorbitols and sorbitol esters, trihydroxystearin; polyhydric alcohols; other ethoxylated derivatives of lipids; and the like.

Oxidation of unsaturated carbons in substances, such as cellulose derivatives, proteins, lecithin and unsaturated hydrocarbons, may lead to rancidity of the skin care composition. Anti-oxidants can be added to minimize or prevent the oxidation process, which enhances the shelf life of the composition. Anti-oxidants useful herein should preferably be mild and non-irritating. Anti-oxidants from natural sources are preferred, such as Vitamin E and derivatives, including tocopherol, tocopherol acetate, mixed tocopherols (available as COVI-OX T-50 or T-70 from Henkel Corp, Ambler, Pa.), and the like.

Safe and effective skin care agents may be incorporated in the skin care composition for use herein. Such materials include Category I and Category III actives as defined by the U.S. Food and Drug Administration's (FDA) Tentative Final Monograph on Skin Protectant Drug Products for Over-the-Counter Human Use (21 C.F.R. § 347). These monographed materials are known to provide multiple skin benefits, such as skin protection, itch prevention, irritation prevention, via various mechanisms. It will be recognized that several of the monographed actives listed below are "emollients" as defined herein. Category I actives presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Category III actives presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like. These monographed materials are known to provide multiple skin benefits, such as skin protectant, itch prevention, irritation prevention, via various mechanisms.

Other skin care agents are suitable for the present invention may include, but are not limited to, pH control agents or proton donating agents, protease inhibitors, enzyme inhibitors, chelating agents, anti-microbials, skin soothing agents and the like. Some nonlimiting examples of these skin care agents are described in co-pending U.S. application Ser. No. 09/041,509, by McOsker et al. filed on Mar. 12, 1998; U.S. application Ser. No. 09/041,232, by Rourke et al filed on Mar. 12, 1998; U.S. application Ser. No. 09/041,266, by Roe et al. and U.S. application Ser. No. 09/041,196, by Underiner et al., both filed on Mar. 12, 1998; Patent Application EP 97/120,699 and EP 97/120,700 both by Polumbo et al. and filed on Nov. 26, 1997;U.S. Pat. No. 5,091,193 issued to Enjolras et al, on Feb. 25, 1992; U.S. Pat. No. 4,556,560 issued to Buckingham on Dec. 3, 1985; U.S. Pat. No. 5,376,655 issued to Imaki et al. on Dec. 27, 1994; U.S. Pat. No. 5,091,193 issued to Enjolras et al. on Feb. 25, 1992; U.S. Pat. No. 3,935,862 issued to Kraskin on Feb. 3, 1976;

U.S. Pat. No. 5,409,903 issued to Polak et al. on Apr. 25, 1995; U.S. Pat. No. 4,556,560 issued to Buckingham on Dec. 3, 1985; all are incorporated by reference herein.

Particularly preferred skin care agents herein include: zinc oxide, talc, starch, allantoin, aloe vera, hexamidine and its salts and derivatives, hexamidine diisethionate, and its salts, triacetin, phytic acid, ethylenediamine tetraacetic acid (EDTA), phenylsulfonyl fluorides such as 4-(2-aminoethyl)-benzenesulfonylfluoride hydrochloride, chitosan, and mixtures thereof.

Suitable rheological agents such as suspending agents or viscosity modifiers, may be need for dispersing and suspending the skin care agents in the compositions. Some of the suspending agents may also function as viscosity enhancing agents. Nonlimiting examples of the suspending agents include treated and untreated silicas (e.g., CAB-O-SIL®, available from Cabot Corp., Tuscola, Ill.), organoclays (e.g., BENTONE®, available from Rheox Inc., Hightstown, N.J.), derivatives of castor oil, metal fatty acid soaps, silicates of calcium, magnesium, magnesium/aluminum, and mixtures thereof, talc, cellulose and modified cellulose, polymeric thickeners, certain anionic surfactants, and the like. Particularly preferred suspending agents are disclosed in co-pending U.S. patent application Ser. No. 09/316,691, filed by Gatto et al, on May 21, 1999, the disclosure of which is herein incorporated by reference.

If water-based skin care compositions are used, emulsifiers may be added for solubilizing the thickening agents and/or suspending agents in the emollients. Suitable emulsifiers are typically hydrophilic surfactants, preferably mild and non-irritating to the skin. For example, nonionic hydrophilic surfactants non-irritating to the skin, and also avoid undesirable effects on any underlying tissue laminate structure. Suitable hydrophilic surfactants, nonionic or other types, are known in the art and may be incorporated in appropriate amounts in the compositions useful herein, particularly preferred surfactants are disclosed in U.S. Pat. No. 5,607,760 issued Mar. 4, 1997; U.S. Pat. No. 5,609,587 issued Mar. 11, 1997; U.S. Pat. No. 5,635,191 issued Jun. 3, 1997; and U.S. Pat. No. 5,643,588 issued Jul. 1, 1997, the disclosures of which are hereby incorporated by reference.

A preservative will also be needed to prevent bacterial growth and odors thereof, particularly in water-based skin care compositions. Suitable preservatives include propyl paraben, methyl paraben, benzyl alcohol, benzalkonium, tribasic calcium phosphate, BHT, or acids such as citric, tartaric, maleic, lactic, malic, benzoic, salicylic, and the like.

Suitable solvents include propylene glycol, glycerine, cyclomethicone, polyethylene glycols, hexalene glycol, diol and multi-hydroxy based solvents.

Suitable vitamins include A, $B_3$, $B_5$, niacinamide, panthenol, C and derivatives, $D_3$, E and derivatives, such as E acetate.

IV. Preparing Compositions

In preparing the compositions used herein, the order and manner of mixing the various components are not particularly critical. It is not necessary to mix the components together at elevated temperatures. It is found that the components may be thoroughly mixed to form a substantially uniform composition at temperatures which range from about 40° C. to about 100° C. Agitation is generally required. And it is found that viscous heat generated from agitation may be sufficient to raise the temperature of the mixture or composition so that a substantially uniform dispersion of components therein can be achieved. Sometimes, external heat may be added. It is preferred that the rheological agent be added to the medium with agitation such that the rheological agent is mixed uniformly and/or activated (i.e., form a rheological structure). Where predispersions are used, the particulate materials and the predispersant are pre-mixed in a separate step before being added to the composition. However, predispersion of zinc oxide or other skin care ingredients are not required. These ingredients can be mixed with the carrier directly under sufficient agitation.

Treating Articles with Compositions

While the compositions of the present invention typically are applied to the skin via a delivery vehicle such as an absorbent article, it is to be understood that these compositions may be used in combination with other delivery vehicles, such as canisters, stick casings, cosmetic pads, sponges, patches, sheet substrates, aerosols, and the like. Nonlimiting examples of such delivery vehicles are described in co-pending U.S. patent application Ser. No. 09/326,149, filed by McOsker et al. on Jun. 4, 1999, U.S. patent application Ser.. No. 09/370,396, filed by McOsker et al. on Aug. 6, 1999, and U.S. Pat. No. 5,000,356, issued to Johnson et al. on Mar. 19, 1991; all are incorporated herein by reference.

In preparing absorbent articles treated with the skin care compositions of the present invention, the skin care composition is applied to the article such that during wear, at least some portion of the composition will transfer from the treated article to the wearer's skin. That is, skin care composition may be applied directly to one or more wearer-contacting surfaces, such as topsheet, backsheet, cuff, side panel, and waist region. The skin care composition may also be applied in alternate locations or via means such that the skin care composition is readily available for transfer from one or more wearer-contacting surfaces during use without intervention by the user/caregiver. Specifically, materials positioned beneath the wearer-contacting surface (such as a secondary layer underlying the topsheet or backsheet, an insertable element inserted into the absorbent article for use during wear of the article, encapsulated compositions, etc). Of course, to effectuate delivery of composition to those body regions most susceptible to contact with feces, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc.

Nonliniting examples of suitable methods include spraying, printing (e.g., flexographic printing), coating (e.g., contact slot coating, gravure coating), extrusion, or combinations of these application techniques, e.g., spraying the skin care composition on a rotating surface, such as a calender roll, that then transfers the composition to the desired portion of the article. The skin care composition can also be applied as a solid or semi-solid material via any of a variety methods; for example, extrusion is suited for skin care composition having an apparent viscosity in the range from about 100,000 centipoise to about 1,000,000 centipoise at the processing temperature.

When applied to the article's topsheet, the manner of applying the composition to the article should preferably be such that the topsheet does not become saturated with the composition, at least in the region corresponding to the liquid discharge region of the article, if the composition is hydrophobic in nature. If the topsheet becomes saturated with the composition in the liquid discharge region, there is a greater potential for the composition to block the topsheet openings, reducing the ability of the topsheet to transmit liquid to the underlying absorbent core. Also, saturation of the topsheet is not required to obtain the skin care benefits. Similarly, saturation of other treated article components may not be necessary or desired to transfer sufficient composition for desired skin benefits. Particularly suitable application methods will apply the composition primarily to the outer surface of the topsheet of the article.

The minimum level of the composition to be applied to the article's wearer-contacting surface is an amount effective for providing the appearance, protective and/or skin conditioning benefits when the composition is delivered to the skin of the wearer pursuant to the present invention. The level of composition applied will depend on various factors, including the article component treated, the relative amount of surface area of the wearer-contacting surface not treated with the composition, the content of the composition and the like. In general, the composition is applied to the article in an amount ranging from about 0.05 mg/in$^2$ (0.0078 mg/cm$^2$) to about 100 mg/in$^2$ (15.6 mg/cm$^2$), preferably from about 0.1 mg/in$^2$ (0.016 mg/cm$^2$) to about 50 mg/in$^2$ (7.8 mg/cm$^2$), more preferably from about 1 mg/in$^2$ (0.156 mg/cm$^2$) to about 25 mg/in$^2$ (3.9 mg/cm$^2$). It is recognized that the skin care compositions are relatively hydrophobic and to be applied to the topsheet of the article without covering the entire topsheet surface. It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels or complete coverage may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

Because the composition is preferably substantially immobilized on the surface of the region treated, relatively small amounts of composition are needed to deliver an effective amount of the active. It is believed that the ability to use low levels to impart the desired skin benefits is due to the fact that the composition is continuously, automatically delivered as articles are worn. As indicated, the ability to use relatively low levels of skin care composition, allows the topsheet of the article to maintain its liquid transfer properties in the liquid discharge region.

The skin care composition containing a active can be applied nonuniformly to the wearer-contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article. As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. (It is understood that the crotch point is determined by placing the absorbent article on a wearer in the intended manner and determining where the crossed filament would contact the article.) With regard to incontinence devices (e.g., diapers, training pants, adult incontinent articles), the length of the crotch region corresponds to 40% of the absorbent article's total length (i.e., in the y-dimension). With regard sanitary napkins, the length of the crotch region corresponds to 80% of the absorbent article's total length. The width of the crotch region is equivalent to the width of the widest absorbent core component as measured at the crotch point. (As used herein, "absorbent core" components are those materials involved with acquiring, transporting, distributing and/or storing body liquids. As such, the term absorbent core does not include the topsheet or backsheet of the absorbent article.) By way of illustration, for an incontinence article having a length of 20 in. and a core width at the crotch point of 4 in., the crotch region is the rectangle, centered on the crotch point, having a length of 8 in. and a width of 4 in.

Surprisingly, while the topsheet or other components comprising the skin care composition are treated nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, friction created during wear time between the wearer's skin and the treated region, warmth generated from wearer to enhance the transfer of the composition, the properties of the composition, the materials which constitute the composition, and the like.

Where the composition is applied nonuniformly, any pattern may be utilized, including, for example, application of small droplets (obtained via, e.g., spraying) discrete dots (obtained via, e.g., gravure printing), stripes that run in the longitudinal or lateral direction of the article (obtained via contact slot coating), spirals that run in the longitudinal or lateral direction, etc., patterned prints, etc. In those embodiments where the topsheet comprises discrete, untreated regions, the percent open area of the region of the topsheet that corresponds to the crotch region of the article can vary widely. (As referred to herein, the "percent open area" of the topsheet is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, "untreated" means a region of the topsheet having less than about 0.01 mg/in$^2$ (0.0016 mg/cm$^2$) of the composition. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired composition effect and the desired liquid handling properties of the topsheet will be dictated largely by the characteristics of the composition (in particular the contents of the composition and the relative hydrophobicity/hydrophilicity properties). One skilled in the art will appreciate that the desired percent open area will be readily determined through routine experimentation.

In general, with compositions that are relatively hydrophobic and are to be applied such that regions of the topsheet are not coated with the composition, the composition is preferably applied to the article topsheet in an amount ranging from about 0.05 mg/in$^2$ (0.0078 mg/cm$^2$) to about 100 mg/in$^2$ (15.6 mg/cm$^2$), preferably from about 0.1 mg/in$^2$ (0.016 mg/cm$^2$) to about 50 mg/in$^2$ (7.8 mg/cm$^2$), more preferably from about 1 mg/in$^2$ (0.156 mg/cm$^2$) to about 25 mg/in$^2$ (3.9 mg/cm$^2$). It will be recognized that for compositions that are relatively hydrophilic, higher add-on levels may be used without adversely impacting liquid handling properties of the topsheet to an unacceptable degree. Of course, for articles having relatively high percent open areas in the crotch, greater add-on levels may be obtainable without adversely affecting liquid handling by the topsheet.

In one preferred embodiment of the present invention, the topsheet of the articles utilized will comprise stripes of the skin care composition that run in the article's longitudinal direction. These longitudinal stripes (or spirals) are separated by longitudinal stripes where little or no skin care composition is applied to the topsheet. In these embodiments, each stripe of composition will typically have a width of from about 0.1 in. to about 0.75 in., more typically from about 0.1 in. to about 0.5 in., and the width of the stripes containing no composition will typically be from about 0.1 in. to about 1 in., more typically from about 0.15 to about 0.5 in. These ranges are applicable to typical infant diaper designs. For larger products such as adult incontinent products, these ranges may be higher.

Skin care composition can also be applied in nonuniform patterns on other article components. In these cases, the open area is calculated by the rectangle defined by the perimeters of the skin care composition.

The composition can be applied to the article at any point during assembly. For example, the composition can be applied to the finished disposable absorbent product before it has been packaged. The composition can also be applied to a given component (e.g., topsheet, cuffs, sides, waist, etc.), at the converting site or by the material supplier, before it is combined with the other raw materials to form a finished disposable absorbent product. Again, the composition can be applied to other zones of the article such that the composition will migrate to one or more wearer-contacting surfaces during use.

The composition is typically applied from a melt thereof to the article. In a preferred embodiment, the composition fully melts at a temperature significantly above room temperature, it is usually applied as a heated composition to the article. Typically, the composition is heated to a temperature in the range from about 35° C. to about 150° C., preferably from 40° C. to about 100° C., prior to being applied to the article. Any skin care active ingredients may be added to the composition prior to or after heating. Special care should be taken when heat-sensitive ingredients are used, for example, protease inhibitors or enzyme inhibitors. If added prior to heating, the temperature to which the composition is heated is selected so as not to denature the inhibitors. Alternatively, the inhibitors may be added to the pre-heated composition when it has cooled to a temperature that does not affect the inhibitors but is still sufficiently liquid to be applied to the article. Once the melted composition has been applied to the article, it is allowed to cool and solidify. Preferably, the application process is designed to aid in the cooling/set up of the composition.

In applying compositions to the articles, contact slot coating, spraying, gravure coating, extrusion coating methods are preferred. One such method involves slot coating of the composition on the topsheet of the article, either before or after the topsheet is assembled with the other raw materials into a finished absorbent article.

Figure 2:
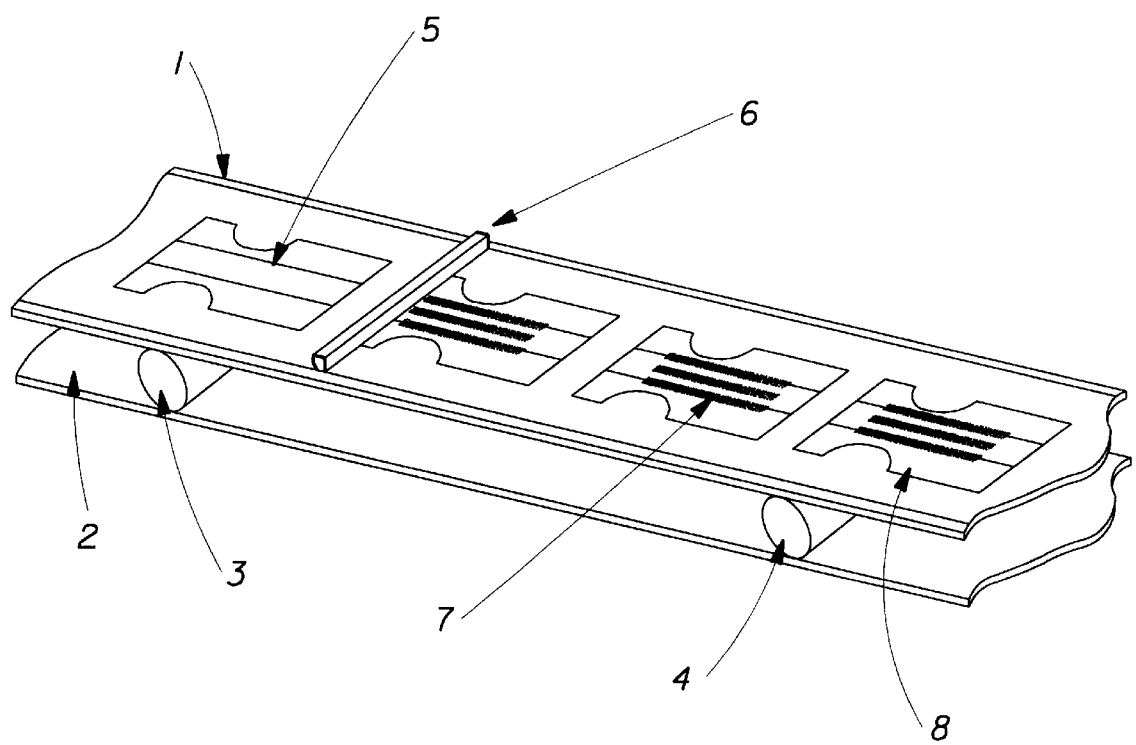
FIG. 2 shows a schematic representation illustrating a preferred process for applying the skin care composition used in the present invention to diaper topsheet and/or cuffs.

FIG. 2 illustrates a preferred method involving continuous or intermittent contact slot coating of the skin care composition onto a diaper topsheet and/or leg cuffs during the converting operation. Referring to FIG. 2, conveyor belt 1 advances in the direction shown by the arrows on turning rolls 3 and 4 and becomes returning conveyor belt 2. Conveyor belt 1 carries non-lotioned diaper 5 to contact slot coating station 6 where the topsheet and/or cuffs patch 7 is coated with a hot, molten (e.g., 170° F. or 77° C.) skin care composition. After leaving slot coating station 6, non-lotioned diaper 5 becomes lotioned diaper 8. The amount of skin care composition transferred to patch 7 is controlled by: (1) the rate at which the molten skin care composition is applied from contact slot coating station 6; and/or (2) the speed at which conveyor belt 1 travels under slot coating station 6.

Figure 3:
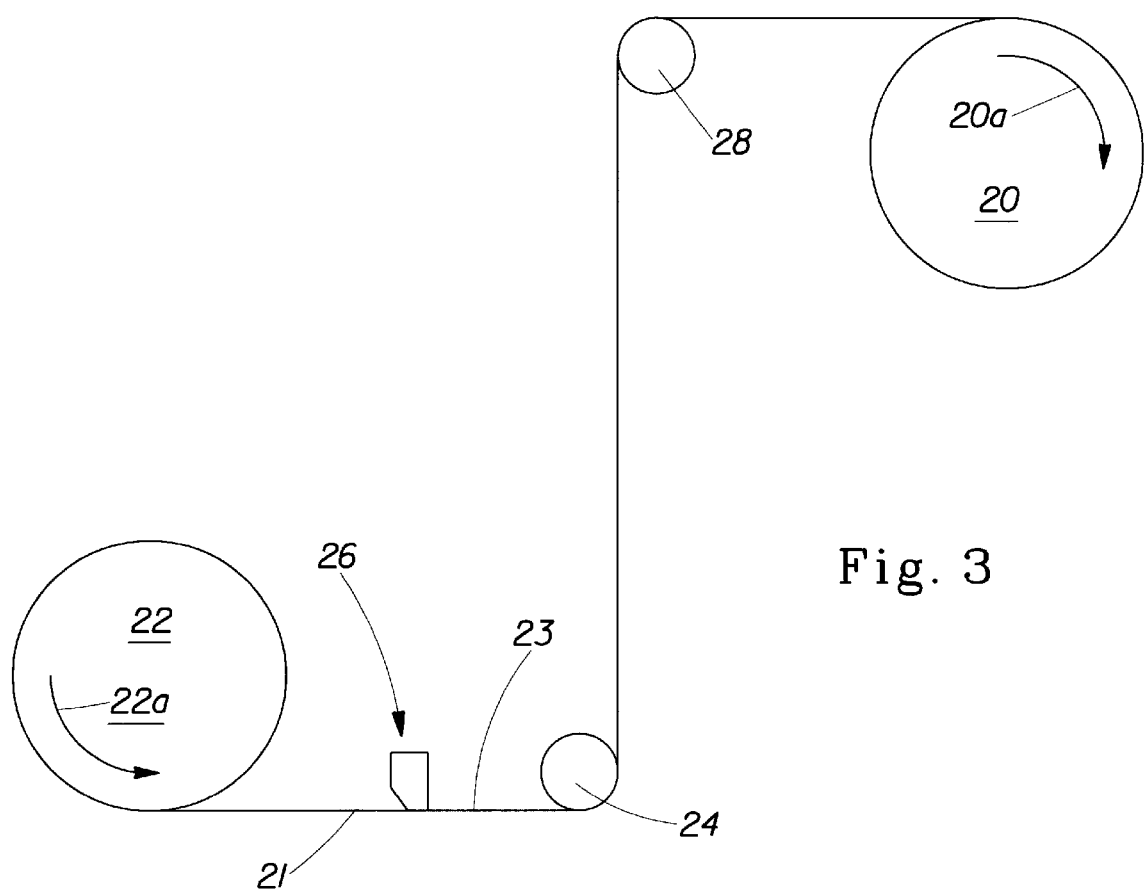
FIG. 3 shows a schematic representation illustrating an alternative process for applying the skin care composition used in the present invention to diaper topsheet and/or cuffs.

FIG. 3 illustrates an alternate preferred method involving contact slot coating of the skin care composition on the diaper topsheet and/or cuffs before the topsheet and/or cuffs are assembled with other raw materials into a finished product. Referring to FIG. 3, a nonwoven web 21 is unwound from parent roll 22 (rotating in the direction indicated by arrow 22a) and advanced to the contact slot coating station 26 where one side of the web is coated with a hot, molten (e.g., 170° F. or 77° C.) skin care composition. After leaving slot coating station 26, nonwoven web 21 becomes a lotioned web indicated by 23. Lotioned web 23 is then advanced around turning roll 24 and turning roll 28, and then wound up on parent roll 20 (rotating in the direction indicated by arrow 20a).

VI. Test Methods

A. Water Vapor Transmission Rate

The Water Vapor Transmission Rate (WVTR) determines the rate of water evaporation through a collagen film treated with a skin care composition on one side. As indicated hereunder, it is a measure of the "breathability" of the skin care composition when the composition is coated on the skin.

Collagen film with a basis weight of 28 gm/m$^2$ (under the designation COFFI, available from Naturin GmbH, Weinhein, Genrany, or from Brechteen Company, Chesterfield, Mich.) is used for this test. The collagen film is equilibrated in a controlled environment (72+/−3° F. and 40+/−10% Relative Humidity) for at least 16 hours prior to testing. A sample of about 50 cm$^2$ is cut from the collagen film and weighed. Sample cutting devices, such as scissors or sample puncher, may be used. Rubber gloves or finger cots are worn when handling the collagen film.

A skin care composition is applied to the collagen film on one side only. Where the collagen film is textured, the composition is applied to the smoother side only. The composition is applied uniformly till the desired loading level is achieved (e.g., around 1.0 mg/cm2). The coated collagen film is weighed and loading level of the skin care composition is determined.

About 10 milliliter of distilled water is added to a suitable reservoir, such as a Fisher Permeability Cup (available from Fisher Scientific, Pittsburgh, Pa.). The coated collagen film is placed over the opening of the reservoir, with the composition treated side facing the distilled water. The coated collagen film sample should be larger than the opening of the reservoir such that it covers the opening of the reservoir. The film sample is tightly affixed to the opening of the reservoir so it acts as a barrier to moisture transport.

After 30 minutes in the controlled environment (72° F. and 40% Relative Humidity), the water evaporation rate through the coated collagen film is determined by a single probe, computer interfaced instrument, such as a DermaLab Evaporimeter (available from DermaLab, Cortex Technology, Denmark). The probe is placed flat on the uncoated (i.e., outward-facing) surface of the collagen film for a designated test time, which typically is about 45 seconds or longer. The evaporation rate should reach a plateau (in about 20 seconds) and remain stable during the remaining test time. If the evaporation rate does not reach a plateau or is unstable, the result is discarded, and the test is repeated. The reported average evaporation rate can be determined once a stable plateau is reached (e.g., the "20 second mean" is a commonly used mean evaporation rate value that is an average of the last 20 seconds of the plateau portion of the test evaporation rate curve).

The loading level of the skin care composition is a variable in the measured water evaporation rate. For example, skin care compositions applied at a level of 0.5 mg/cm2 typically exhibit a higher water evaporation rate than when applied at a level of 1.0 mg/cm2. Therefore, when comparing the water vapor transmission rate of different skin care compositions, it is necessary that the skin care composition application level be the same.

B. Barrier Property Testing

A Methylene Blue Dye Test is used to assess the moisture barrier properties of skin care compositions used herein.

Collagen film (such as that described herein for the WVTR test) is preconditioned in a controlled environment (72+/−3° F. and 40+/−10% Relative Humidity) for at least 16 hours prior to testing. A skin care composition is applied to the smooth side (where applicable) of the collagen film uniformly, till the desired loading level is achieved (e.g., about 1.0 mg/cm2). The collagen film is laid flat on a suitable surface and methylene blue solution (0.5 gm of methylene blue dye in 100 mL of distilled water) is added with a pipet onto the collagen film surface within a circular area of approximately 5 cm². The add-on level of methylene blue solution should be carefully controlled so that it does not spread beyond the area of the collagen film.

After about 30 minutes, the methylene blue solution is removed from the surface of the collagen film by blotting it carefully with paper towel. The collagen film is allowed to dry for about 5 minutes. The "dried" collagen film, a sheet of white paper (e.g., standard printer paper), and a clear vinyl sheet protector having a black sheet insert (e.g., Avery® 5VY81 1) are assembled into a multi-layered structure to provide a constant background for the chromameter measurement as well as to keep the skin care composition from direct contact with the instrument probe. The assembly is as follows (from top to bottom): a clear vinyl sheet, the "dried" collagen film with the smooth or treated side up, a sheet of white paper, a sheet of black paper, and a clear vinyl sheet.

The stain on the collagen film is measured by a Colorimeter or Chromameter (available from Minolta, Ramsey, N.J., or Acaderm, Menlo Park, Calif.) and is expressed as "b" value in Hunter's L•a•b color coordinates. Under Hunter's system, "a" coordinate ranges from red (positive value) to green (negative value); "b" coordinates ranges from yellow (positive value) to blue (negative value); and "L" coordinate ranges from white (100 value) to black (0 value). See Billmeyer and Saltzman, "Principles of Color Technology", second edition (1981), Wiley & Sons, pp. 59–60. A negative "b" value indicates blue coloration of the test collagen film, which is the result of methylene blue solution penetration through the skin care composition covering the collagen film. Therefore, a more negative the "b" value indicates a poorer water barrier property of the skin care composition.

VII. EXAMPLES

The following examples further describe and demonstrate embodiments within the scope of the present invention. The examples are given solely for the purpose of illustration and are not to be construed as limitations of the present invention, as many variations thereof are possible without departing form the spirit and scope of the invention.

Each of the skin care composition examples described below is formed by combining and mixing the ingredients using technology known in the art, then deposited on the topsheet of an absorbent article via a contact slot coater as disclosed herein. For example, a hot melt adhesive applicator head having multiple slots (Meltex EPI 1, available from Nordson Corp., Atlanta, Ga.) is suitable for use in the present invention. The composition is placed into a heated tank operating at a temperature of about 77° C. (i.e., about 170° F.). The composition is subsequently applied with a contact applicator onto the topsheet and/or cuffs of a desired article in a striped pattern where the stripes run in the article's longitudinal direction. Specifically, 5 stripes are applied, each stripe measuring about 0.25 inch in width (i.e., the substrate's lateral direction), about 11.7 inches in the longitudinal direction of the substrate, and at an add-on level of about 15.5 mg/in² (2.4 mg/cm²). The distance between the stripes is about 0.31 inch

Example 1

The following is an example of a skin care composition useful for coating a desired article in accordance with the present invention. The composition is formed by combining and mixing the ingredients using technology known in the art.

| Ingredients | Weight % |
| --- | --- |
| Triglyceride | 26 |
| Squalane | 9 |
| Cholesterol Hydroxystearate | 33 |
| Cholesterol | 9 |
| Petrolatum | 12 |
| Glyceryl Linoleate | 7 |
| Sucrose Ester Fatty Acid | 4 |

Example 2

The following is an example of another skin care composition used in the present invention as in Example 1. The composition is formed by combining and mixing the ingredients using technology known in the art.

| Ingredients | Weight % |
| --- | --- |
| Glyceryl Linoleate (Dimodan ®) | 8 |

-continued

| Ingredients | Weight % |
|---|---|
| Cholesterol | 25 |
| Canola Oil (Lipovol ® CAN) | 25 |
| Petrolatum (Perfecta ®) | 15 |
| Squalane (Fitoderm ®) | 12 |
| Behenyl Alcohol (Lanette ® 22) | 12 |
| Wax (Multiwax ® W-445) | 3 |

Wherein Dimodan® is available from Danisco Ingredients, (Copenhagen, Denmark); cholesterol is available from Croda, Inc., Parsippany, N.J.; Lipovol® is available from Lipo Chemicals, Paterson, N.J.; Perfecta® is available from Witco Corp., Greenwich, Conn.; Fitoderm® is available from Hispano Quimica, Barcelona, Spain; Lanette® is available from Henkel Corp., Ambler, Pa.;

and Multiwax® is available from Witco Corp., Greenwich, Conn..

Example 3

The following is an example of a skin care composition used in the present invention as in Example 1. The composition is formed by combining and mixing the ingredients using technology known in the art.

| Ingredients | Weight % |
|---|---|
| Caprylic/Capric Triglyceride (Myritol ® 318) | 17.1 |
| Cholesterol | 10 |
| Super Sterol Ester ® | 8.5 |
| Petrolatum (Perfecta ®) | 20 |
| Acetylated Lanolin (Acylan ®) | 4.3 |
| Squalane (Fitoderm ®) | 8.5 |
| Behenyl Alcohol (Lanette ® 22) | 20 |
| Wax (Multiwax ® W-445) | 3 |
| Octyldodecyl Stearoyl Stearate (Ceraphyl ® 847) | 8.5 |
| Mixed Tocopherols (COVI-OX ® T-50) | 0.2 |

Wherein Myritol®, Lanette® and COVI-OX® are available from Henkel Corp., Ambler, Pa.;

cholesterol, Super Sterol Ester® and Acylan® are available from Croda, Inc., Parsippany, N.J.; Perfecta® is available from Witco Corp., Greenwich, Conn.; Fitoderm® is available from Hispano Quimica, Barcelona, Spain; Multiwax® is available from Witco Corp., Greenwich, Conn.; and Ceraphyl® is available from ISP Van Dyk, Belleville, N.J.

Example 4

The following are examples of skin care compositions used in the present invention as in Example 1. The compositions are formed by combining and mixing the ingredients of each column using technology known in the art.

| | EXAMPLES | | |
|---|---|---|---|
| INGREDIENTS | 4a Wt % | 4b Wt % | 4c Wt % |
| Caprylic/Capric Triglyceride (Myritol ® 318) | 17.1 | 4 | 4 |
| Cholesterol | 10 | 10 | 10 |
| Super Sterol Ester ® | 8.5 | 8.5 | 8.5 |
| Petrolatum (Perfecta ®) | 20 | 20 | 20 |
| Acetylated Lanolin (Acylan ®) | 4.3 | 4.3 | 4.3 |
| Squalane (Fitoderm ®) | 8.5 | 4 | 4 |
| Behenyl Alcohol (Lanette ® 22) | 20 | 20 | 20 |
| Wax (Multiwax ® W-445) | 3 | 3 | 3 |
| Octyldodecyl Stearoyl Stearate (Ceraphyl ® 847) | 3.15 | | |
| Isostearyl Neopentanoate (Ceraphyl ® 375) | 5.35 | | |
| Diisopropyl Adipate (Ceraphyl ® 230) | | 25 | |
| Isononyl Isononanoate (Salacos ® 99) | | | 25 |
| Mixed Tocopherols (COVI-OX ® T-50) | 0.2 | 0.2 | 0.2 |
| Fumed Silicas (Cab-O-Sil ® TS-720) | | 4 | 4 |

Wherein Myritol®, Lanette® and COVI-OX® are available from Henkel Corp., Ambler, Pa.; cholesterol, Super Sterol Ester® and Acylan® are available from Croda, Inc., Parsippany, N.J.; Perfecta® is available from Witco Corp., Greenwich, Conn.; Fitoderm® is available from Hispano Quimica, Barcelona, Spain; Multiwax® is available from Witco Corp., Greenwich, Conn.; Ceraphyls® are available from ISP Van Dyk, Belleville, N.J.; and Cab-O-Sil® is available from Cabot Corp., Tuscola, Ill.

Example 5

The following is an example of a skin care composition used in the present invention as in Example 1. The composition is formed by combining and mixing the ingredients using technology known in the art.

| Ingredients | Weight % |
|---|---|
| Caprylic/Capric Triglyceride (Myritol ® 318) | 10.0 |
| Cholesterol | 8 |
| Super Sterol Esters ® | 11.9 |
| Petrolatum (Perfecta ®) | 30 |
| Acetylated Lanolin (Acylan ®) | 4.0 |
| Squalane (Fitoderm ®) | 8 |
| Behenyl Alcohol (Lanette ® 22) | 15 |
| Wax (Multiwax ® W-445) | 3 |
| Mixed Tocopherols (COVI-OX ® T-50) | 0.1 |
| Triacetin (Priacetin ®) | 10 |

Wherein Myritol®, Lanette® and COVI-OX® are available from Henkel Corp., Ambler, Pa.; cholesterol, Super Sterol Ester® and Acylan® are available from Croda, Inc., Parsippany, N.J.; Perfecta® is available from Witco Corp., Greenwich, Conn.; Fitoderm® is available from Hispano Quimica, Barcelona, Spain; Multiwax® is available from Witco Corp., Greenwich, Conn.; and Priacetin® is available from Unichema, Netherlands.

Example 6

The following is a comparison of barrier property and water vapor transmission rate (WVTR) of (i) an untreated collagen film, which simulates untreated skin, (ii) collagen films covered by comparative compositions 6a and 6b, and (iii) collagen films covered by compositions 6c, 4a, 4b, 4c, and 5 of the present invention. The compositions are formed by combining and mixing the ingredients using technology known in the art.

| Composition | Barrier Property (Hunter's "b" Value) | Water Vapor Transmission Rate WVTR (gm/m2/hr) |
|---|---|---|
| Untreated Collagen | −42.57 | 17.78 |
| 6a | −2.86 | 0.01 |
| 6b | −1.67 | 0.03 |
| 6c | −3.76 | 1.94 |
| 4a | −2.17 | 3.01 |
| 4b | −1.61 | 3.85 |
| 4c | −2.21 | 8.11 |
| 5 | −2.98 | 2.85 |
| 6 | −13.4 | 6.10 |

Composition 6a is 58.5 wt % petrolatum and 41.5 wt % stearyl alcohol; composition 6b is 46 wt % petrolatum, 29 wt % behenyl alcohol, and 25 wt % isononyl isononanoate; and formulation 6c is 46 wt % petrolatum, 29 wt % behenyl alcohol, and 25 wt % diusopropyl adipate; wherein petrolatum is available as Perfecta® from Witco Corp., Greenwich, Conn.; stearyl alcohol is available as CO1879 from Procter & Gamble Co., Cincinnati, Ohio; behenyl alcohol is available as Lanette® 22 from Henkel, Ambler, Pa.; isononyl isononanoate is available as Salacos® 99 from Ikeda Corp., Island Park, N.Y.; and diisopropyl adipate is available as Ceraphyl® 230 from ISP Van Dyk, Belleville, N.J.

The results show skin care composition such as composition 6a has excellent barrier property but is occlusive (i.e., minimal WVTR). The results also show that composition 6b, which incorporates a slightly branched permeability agent such as branched fatty acid esters into composition 6a, improves breathability or non-occlusiveness of the composition but still does not provide desired breathability. Composition 6c which incorporates a highly branched fatty acid ester improves breathability while maintaining the barrier properties of the composition. The results further show that compositions 4a, 4b, 4c, and 5 have improved breathability and still maintain excellent barrier property.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article for applying a skin care composition to the skin, said article comprising a delivery vehicle and a skin care composition disposed on at least a portion of said delivery vehicle, said skin care composition having:
   (a) a semi-solid or solid consistency at 20° C.;
   (b) a Water Vapor Permeation Rate of at least about 0.1 gm/m$^2$ /hr; and
   (c) a Hunter b value in the Methylene Blue Dye Barrier Property Test ranging from about 5 to about −25.

2. The article of claim 1 wherein said skin care composition has a Water Vapor Permeation Rate of at least about 1 gm/m$^2$/hr and a Hunter b value from about 5 to about −15.

3. The article of claim 1 wherein said skin care composition has a Water Vapor Permeation Rate of at least about 10 gm/m$^2$/hr and a Hunter b value from about 5 to about −5.

4. The article of claim 1 wherein said delivery vehicle is selected from the group consisting of absorbent articles, canisters, stick casings, cosmetic pads, sponges, patches, sheet substrates, aerosols, and combinations thereof.

5. The article of claim 1 wherein said delivery vehicle is an absorbent article and said portion of the absorbent article is a surface selected from the group consisting of a topsheet, a backsheet, a cuff, a side panel, a waist region, a secondary layer underlying the topsheet, a secondary layer underlying the backsheet, an insertable element inserted into the absorbent article for use during wear of the article, and combinations thereof.

6. The article of claim 5 wherein said absorbent article is selected from the group consisting of diapers, training pants, sanitary napkins, pantiliners, incontinence articles, diaper holders, and combinations thereof.

7. The article of claim 5 wherein said portion comprises more than one surface and a first skin care composition is disposed on said surfaces.

8. The article of claim 5 wherein said portion comprises a second skin care composition disposed on at least one surface.

9. The article of claim 1 wherein said skin care composition ranges from about 0.05 mg/in$^2$ to about 100 mg/in$^2$.

10. The article of claim 1 wherein said skin care composition comprises:
   (a) from about 5 to about 95% by weight of a emollient;
   (b) from about 1 to about 95% by weight a permeability agent; and
   (c) from about 5 to about 95% by weight an immobilizing agent.

11. The article of claim 10 wherein said emollient comprises a material selected from the group consisting of petroleum-based emollients; fatty acid esters; polyol polyesters; fatty alcohol ethers; sterols and sterol esters, and their derivatives; triglycerides; glyceryl esters; ceramides; and mixtures thereof.

12. The article of claim 11 wherein said emollient is a petroleum based emollient selected from the group consisting of straight chain paraffins, mineral oil, petrolatum, and mixtures thereof.

13. The article of claim 10 wherein said emollient comprises:
   (i) from about 1 to about 40% by weight of the emollient, a sterol;
   (ii) from about 1 to about 90% by weight of the emollient, a sterol ester;
   (iii) from about 1 to about 90% by weight of the emollient, a triglyceride; and
   (iv) from about 1 to about 90% by weight of the emollient, a petroleum-based emollient;
wherein said weight ratio of sterol to petroleum-based emollient is from about 1:1 to about 1:4.

14. The article of claim 13 wherein said sterol is selected from the group consisting of cholesterol, ergosterol, sitosterol, cholecalciferol, phytosterols, soy sterols, tall oil sterols, lanosterols, other sterols in lanolin and hydrogenated lanolin, acetylated lanolin, and mixtures thereof; said sterol ester is selected from the group consisting of $C_2$–$C_{30}$ acid cholesteryl esters, $C_2$–$C_{30}$ acid ergosteryl esters, $C_2$–$C_{30}$ acid sitosteryl esters, $C_2$–$C_{30}$ acid cholecalciferyl esters, $C_2$–$C_{30}$ acid phytosteryl esters, $C_2$–$C_{30}$ acid soy steryl esters, $C_2$–$C_{30}$ acid tall oil steryl esters, $C_2$–$C_{30}$ acid lanosteryl esters, $C_2$–$C_{30}$ acid hydrogenated lanosteryl esters, $C_2$–$C_{30}$ acid acetylated lanosteryl esters, and mixtures thereof; and said triglyceride is selected from the group consisting of synthetic $C_8$–$C_{36}$ fatty acid triglycerides, vegetable oils, hydrogenated vegetable oils and waxes, animal oils, and mixtures thereof.

15. The article of claim 13 wherein said free sterol is selected form the group consisting of cholesterol, acetylated lanolin, lanosterol, and mixtures thereof; said sterol ester is a mixture of $C_{10}$–$C_{30}$ fatty acid cholesterol esters and $C_{10}$–$C_{30}$ fatty acid lanosterol esters; said triglyceride is a mixture of capric acid triglycerides and caprylic acid triglycerides; and said petroleum-based emollient is petrolatum.

16. The article of claim 10 wherein said permeability agent is selected from the group consisting of $C_7$–$C_{40}$ branched hydrocarbons, branched chain aliphatic esters, phospholipids, polysiloxanes, and mixtures thereof.

17. The article of claim 16 wherein said permeability agent is selected from the group consisting of isoparaffins, squalane, squalene, diusopropyl adipate, octyldodecyl stearoyl stearate, isononyl isononanoate, isostearyl isononanoate, octyl palmitate, octyl hydroxystearate, stearyl heptanoate, cetearyl octanoate, butyl octanol, 2-ethylhexyl-12-hydroxy stearate, decyl oleate, dioctyl adipate, dioctyl succinate, isocetyl stearate, octyl cocoate, lecithin, cephalin, sphingomyelin, a substituted polymethylsiloxane having at least one functional group selected from the group consisting of methyl, phenyl, amino, other alkyl, carboxyl, hydroxyl, ether, polyether, aldehyde, ketone, amide, ester, thiol groups, and mixtures thereof.

18. The article of claim 17 wherein said permeability agent is selected from the group consisting of diisopropyl adipate, isononyl isononanoate, squalane, squalene, isoparaffins, lecithin, polydimethylsiloxane, and mixtures thereof.

19. The article of claim 10 wherein said immobilizing agent is selected from the group consisting of waxes, polyhydroxy fatty acid esters, polyhydroxy fatty acid amides, $C_{14}$–$C_{22}$ fatty alcohols, $C_{12}$–$C_{22}$ fatty acids, $C_{12}$–$C_{22}$ fatty alcohol ethoxylates having an average degree of ethoxylation of about 2 to about 30, $C_8$–$C_{30}$ acid glyceryl esters, solid polyol polyesters, and mixtures thereof.

20. The article of claim 19 wherein said immobilizing agent is selected from the group consisting of ozokerite wax, jojoba wax, candelilla wax, carnauba wax, beeswax, paraffin wax, ceresin wax, esparto, ouricuri, rezowax, silicone wax, cetyl alcohol, stearyl alcohol, cetearyl alcohol, behenyl alcohol, and mixtures thereof.

21. The article of claim 10 wherein said skin care composition further comprises a skin care agent selected from the group consisting of Monographed Category I ingredients, Monographed Category III ingredients, enzyme inhibitors, protease inhibitors, chelating agents, antimicrobials, proton donating agents, skin soothing agents, vitamins, and mixtures thereof.

22. The article of claim 21 wherein said skin care agent is selected from the group consisting of zinc oxide, talc, starch, aloe vera, allantoin, hexamidine and its derivatives and salts, hexamidine diisethionate and its salts, triacetin, phytic acid, ethylenediamine tetraacetic acid (EDTA), phenylsulfonylfluorides, chitosan, and mixtures thereof.

23. The article of claim 10 wherein said skin care composition further comprises an anti-oxidant selected from the group consisting of tocopherol, tocopherol acetate, mixed tocopherols, and mixtures thereof.

24. The article of claim 10 wherein said skin care composition further comprising a material selected from the group consisting of water, surfactants, skin care agents, humectants, anti-oxidants, viscosity modifiers, suspending agents, pH buffering systems, perfumes, soothing agents, pigments, disinfectants, antibacterial actives, pharmaceutical actives, film formers, deodorants, opacifiers, astringents, solvents, and mixtures thereof.

25. The article of claim 10 wherein said skin care composition further comprises a suspending agent selected from the group consisting of fumed silicas, treated fumed silicas, organoclays, and mixtures thereof.

26. The article of claim 1 wherein said skin care composition comprises:
   (a) from about 1% to about 50% a petroleum-based emollients;
   (b) from about 1% to about 25% a free sterol;
   (c) from about 1% to about 50% a sterol ester;
   (d) from about 1% to about 40% a triglyceride;
   (e) from about 5% to about 50% a permeability agent; and
   (f) from about 5% to about 50% a fatty alcohol.

27. The article of claim 26 wherein said petroleum based emollient is petrolatum, the free sterol is cholesterol, the sterol ester is a mixture of $C_{10}$–$C_{30}$ fatty acid cholesterol esters and $C_{10}$–$C_{30}$ fatty acid lanosterol esters, the triglyceride is a mixture of caprylic/capric acid esters, the permeability agent is a mixture of squalane and diisopropyl adipate, and the fatty alcohol is behenyl alcohol.

28. The article of claim 26 wherein said optional other ingredients are at least one material selected from the group consisting of water, surfactants, skin care agents, humectants, anti-oxidants, viscosity modifiers, suspending agents, pH buffering systems, perfumes, soothing agents, pigments, disinfectants, antibacterial actives, pharmaceutical actives, film formers, deodorants, opacifiers, astringents, solvents, and mixtures thereof.

29. An article to be placed in contact with the skin for applying a skin care composition to the skin, said article comprising a delivery vehicle and a skin care composition disposed on at least a portion of said delivery vehicle, said skin care composition comprising:
   (a) from about 5 to about 95% by weight of a emollient selected from the group consisting of petroleum-based emollients; fatty acid esters; polyol polyesters; fatty alcohol ethers; sterols and sterol esters, and their derivatives; triglycerides; glyceryl esters; ceramides; and mixtures thereof;
   (b) from about 1 to about 95% by weight a permeability agent selected from the group consisting of $C_7$–$C_{40}$ branched hydrocarbons, branched chain aliphatic esters, phospholipids, polysiloxanes, and mixtures thereof; and
   (c) from about 5 to about 95% by weight an immobilizing agent selected from the group consisting of waxes, polyhydroxy fatty acid esters, polyhydroxy fatty acid amides, $C_{14}$–$C_{22}$ fatty alcohols, $C_{12}$–$C_{22}$ fatty acids, $C_{12}$–$C_{22}$ fatty alcohol ethoxylates having an average degree of ethoxylation of about 2 to about 30, $C_8$–$C_{30}$ acid glyceryl esters, solid polyol polyesters, and mixtures thereof.

30. The article of claim 29 wherein said delivery vehicle is selected from the group consisting of absorbent articles, canisters, stick casings, cosmetic pads, sponges, patches, sheet substrates, aerosols, and combinations thereof.

31. The article of claim 30 wherein said delivery vehicle is an absorbent article and said portion of the absorbent article is a surface selected from the group consisting of a topsheet, a backsheet, a cuff, a side panel, a waist region, a secondary layer underlying the topsheet, a secondary layer underlying the backsheet, an insertable element inserted into the absorbent article for use during wear of the article, and combinations thereof.

32. The article of claim 31 wherein said absorbent article is selected from the group consisting of diapers, training pants, sanitary napkins, pantiliners, incontinence articles, diaper holders, and combinations thereof.

* * * * *

UNITED STATES PATENT AND TRADEMARK OFFICE
CERTIFICATE OF CORRECTION

PATENT NO.    : 6,153,209
DATED         : November 28, 2000
INVENTOR(S)   : Vega et al.

It is certified that error appears in the above-identified patent and that said Letters Patent is hereby corrected as shown below:

Column 2,
Line 36, delete "epidernis" and insert therefor -- epidermis --.

Column 4,
Line 36, delete "Permeation" and insert therefore -- Transmission --.

Column 7,
Line 8, delete "backshect" and insert therefore -- backsheet --.

Column 8,
Line 31, delete "H-203 1" and insert therefore -- H-2031 --.

Column 11,
Line 38, delete "bc"and insert therefore -- be --.

Column 13,
Line 12, delete "5,569,23 1" and insert therefore -- 5,569,231 --.

Column 15,
Line 24, delete "theological" and insert therefore -- rheological --.

Column 18,
Line 10, after "thereof" insert therefore -- . -- (a period).

Column 23,
Line 9, after "skin." insert a paragraph break.

Column 26,
Line 2, delete "comeum" and insert therefore -- corneum --.

Column 28,
Line 48, delete "Nonliniting" and insert therefore -- Nonlimiting --.

Column 32,
Line 49, delete "Genrany" and insert therefore -- Germany --.

Column 33,
Line 53, delete "5VY81 1" and insert therefore -- 5VY811 --.

UNITED STATES PATENT AND TRADEMARK OFFICE
CERTIFICATE OF CORRECTION

PATENT NO.    : 6,153,209
DATED         : November 28, 2000
INVENTOR(S)   : Vega et al.

It is certified that error appears in the above-identified patent and that said Letters Patent is hereby corrected as shown below:

Column 34,
Line 1, delete "valuc" and insert therefore -- value --.
Line 23, delete "EPI 1" and insert therefore -- EP11 --.

Column 35,
Line 42, delete the line break and continue with "cholesterol,".

Column 37,
Please delete last line of the Table, "6" "-13.4" and "6.10".
Line 19, delete "diusopropyl" and insert therefore -- diisopropyl --.
Line 58, delete "Permeation" and insert therefore -- Transmission --.
Line 59, delete "gm/m$^2$ /hr" and insert therefore -- gm/m$^2$/hr -- (deleting the space before "/hr").
Line 63, delete "Permeation" and insert therefore -- Transmission --.
Line 66, delete "Permeation" and insert therefore -- Transmission --.

Column 39,
Line 5, delete "form" and insert therefore -- from --.
Line 16, delete "diusopropyl" and insert therefore -- diisopropyl --.

Signed and Sealed this

Twenty-ninth Day of October, 2002

Attest:

Attesting Officer

JAMES E. ROGAN
Director of the United States Patent and Trademark Office